United States Patent
Potyrailo et al.

(10) Patent No.: US 11,408,874 B2
(45) Date of Patent: Aug. 9, 2022

(54) SENSING SYSTEM AND METHOD

(71) Applicant: General Electric Company, Schenectady, NY (US)

(72) Inventors: Radislav Alexandrovich Potyrailo, Niskayuna, NY (US); Chistopher Calvert, Belfast (GB); Martin Duffy, Belfast (GB); Craig Mack, Belfast (GB); Philip McConnell, Belfast (GB)

(73) Assignee: General Electric Technology GmbH, Baden (CH)

( * ) Notice: Subject to any disclaimer, the term of this patent is extended or adjusted under 35 U.S.C. 154(b) by 215 days.

(21) Appl. No.: 16/710,273

(22) PCT Filed: Jun. 13, 2017

(86) PCT No.: PCT/US2017/037123
§ 371 (c)(1),
(2) Date: Dec. 11, 2019

(87) PCT Pub. No.: WO2018/231196
PCT Pub. Date: Dec. 20, 2018

(65) Prior Publication Data
US 2020/0191761 A1  Jun. 18, 2020

(51) Int. Cl.
G01N 33/00 (2006.01)
G01N 27/12 (2006.01)
G01N 33/28 (2006.01)

(52) U.S. Cl.
CPC ....... *G01N 33/0062* (2013.01); *G01N 27/122* (2013.01); *G01N 33/0032* (2013.01);
(Continued)

(58) Field of Classification Search
CPC ........... G01N 33/2841; G01N 33/0032; G01N 33/0062; G01N 33/0073; G01N 2033/0068; G01N 27/122
See application file for complete search history.

(56) References Cited

U.S. PATENT DOCUMENTS

| 5,417,821 A | 5/1995 | Pyke |
| 5,602,324 A | 2/1997 | Yangida |

(Continued)

FOREIGN PATENT DOCUMENTS

KR  101734329  5/2017

OTHER PUBLICATIONS

Carmen C. Mayorga-Martinez, et al., "Metallic TT-WS2 for Selective Impedimetric Vapor Sensing", Advanced Functional Materials, 2015, 25, pp. 5611-5616.

(Continued)

*Primary Examiner* — Paul M. West
(74) *Attorney, Agent, or Firm* — Eversheds Sutherland (US) LLP

(57) ABSTRACT

A system for analysis of at least one analyte gas present in an insulating fluid of an electrical transformer includes a gas sensor in operational contact with at least one analyte gas from an insulating fluid to provide multiple responses from the sensor. One or more processors are configured to receive the multiple responses during exposure of the sensor to the analyte gas from the insulating fluid representative of a concentration of the analyte gas present in the insulating fluid. The processors are configured to select one or more responses of the multiple responses that provide rejection of interfering gases, resolution between gases, improved low detection range of the analyte gas, improved high detection range of the analyte gas, improved response linearity of the analyte gas, improved dynamic range of measurements of the analyte gas, or one or more combinations thereof compared to non-selected responses from the sensor.

19 Claims, 31 Drawing Sheets

(52) U.S. Cl.
CPC ..... *G01N 33/0073* (2013.01); *G01N 33/2841* (2013.01); *G01N 2033/0068* (2013.01)

(56) References Cited

U.S. PATENT DOCUMENTS 6,387,329 B1 * 5/2002 Lewis ................ G01N 15/0826
422/83
2015/0115983 A1 4/2015 Potyrailo

OTHER PUBLICATIONS

PCT International Search Report dated Oct. 4, 2017.
International Preliminary Report on Patentability for corresponding International Application No. PCT/US2017/037123 dated Dec. 26, 2019. (9 pages).
EP search report based on application No. 17733676.1, dated Aug. 11, 2020, pp. 1-3.

* cited by examiner

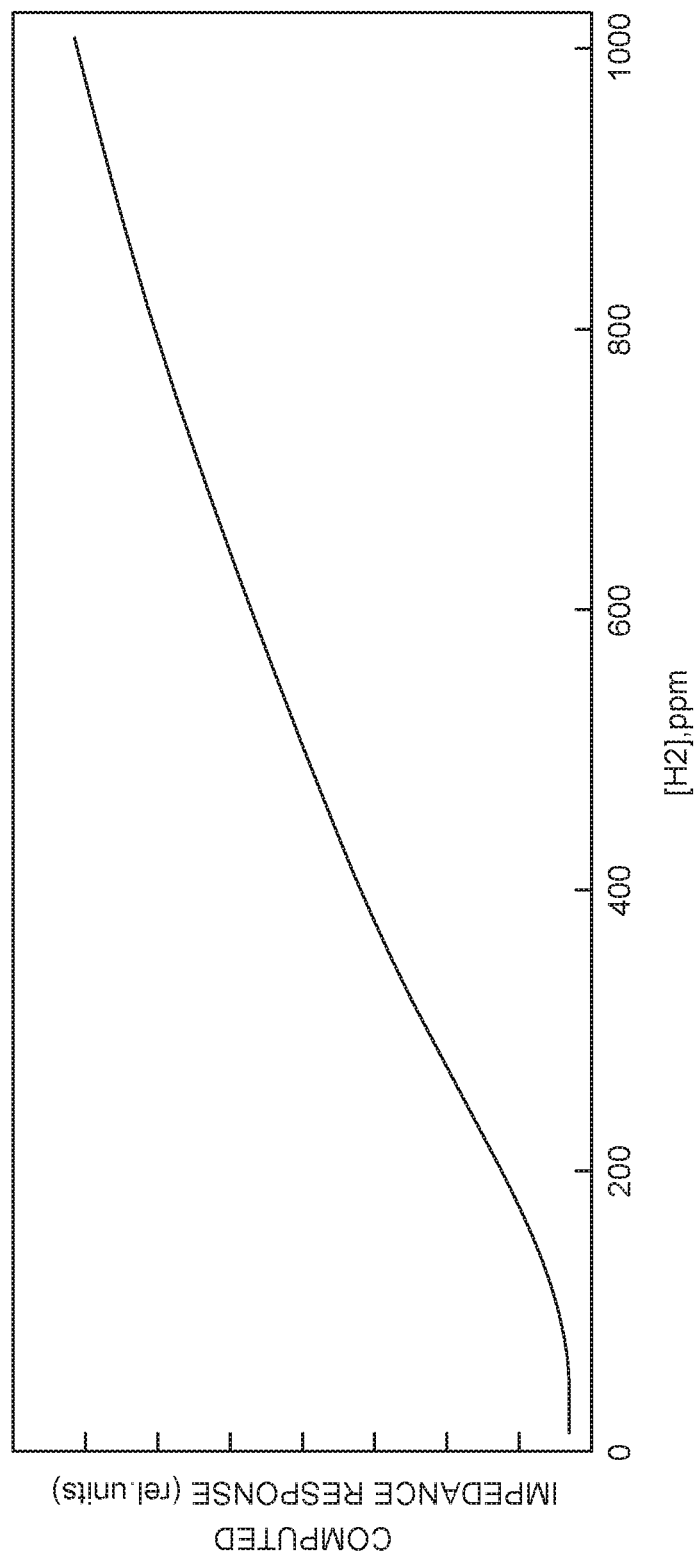

SENSING SYSTEM AND METHOD

CROSS-REFERENCE TO RELATED APPLICATIONS

This application claims priority to International Patent Application PCT/US2017/037123, filed Jun. 13, 2017. The entire disclosure of this application is incorporate herein by reference.

FIELD

One or more embodiments are disclosed that relate to systems and methods for sensing gases.

BACKGROUND

Dissolved gas analysis (DGA) of transformer oil is used for diagnostic measurements of transformer health and prognosis. Concentrations of dissolved gases in oil are measured at the part-per-million (ppm) level, with target gases such as carbon monoxide CO, carbon dioxide $CO_2$, hydrogen $H_2$, methane $CH_4$, acetylene $C_2H_2$, ethylene $C_2H_4$, ethane $C_2H_6$, or the like. Current DGA systems use a method to extract gas from oil (e.g. headspace or membrane) and then measure in the gas phase to infer the ppm concentration in oil. Examples of key existing technologies for the gas determination and sensing are gas chromatography and infrared spectroscopy. To selectively measure the required fault gases, the extraction and gas sensor components can be expensive and complex, have many moving parts, can have a wide range of failure modes or performance challenges, or the like.

Conventional sensors for industrial fluids such as industrial gases are non-selective devices exhibiting significant gas cross-sensitivity and thus, low gas selectivity. The origin of this limitation of conventional sensors of being non-selective is in the conflicting requirements for sensor selectivity versus reversibility. The full and fast reversibility of sensor response is achieved via weak interactions between the analyte and the sensing film, whereas the high selectivity of sensor response is achieved via strong interactions between the analyte gas and the sensing film.

BRIEF DESCRIPTION

In one embodiment, a system for analysis of at least one analyte gas present in an insulating fluid of an electrical transformer includes a gas sensor configured to be in operational contact with at least one analyte gas from an insulating fluid and to provide multiple responses from the sensor. The system includes one or more processors configured to receive the multiple responses from the sensor during exposure of the sensor to the at least one analyte gas from the insulating fluid. The multiple responses representative of a concentration of the at least one analyte gas present in the insulating fluid. The one or more processors are configured to select one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

In one embodiment, a method for analyzing at least one analyte gas present in an insulating fluid of an electrical transformer includes providing multiple responses from a multivariable gas sensor configured to be in operational contact with insulating fluid having at least one analyte gas. The method includes receiving with one or more processors the multiple responses from the sensor during exposure of the sensor to the insulating fluid. The multiple responses representative of a concentration of the at least one analyte gas present in the insulating fluid. The method includes selecting with the one or more processors one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

In one embodiment, a system includes an impedance gas sensor configured to be in contact with a sample having one or more analyte gases therein. The impedance sensor including electrodes and a sensing region circuit having a sensing material. The electrodes configured to apply electrical stimuli to the sensing material at one or more different frequencies. The system includes one or more processors configured to receive an electrical signal from the sensor that is representative of an impedance of the sensing material during exposure of the sensing material to the sample at the one or more different frequencies. The impedance is representative of a concentration of an analyte gas of interest of the one or more analyte gases in the sample. The one or more processors are configured to select a frequency of the one or more different frequencies at which the electrodes of the sensor are to apply the electrical stimuli to the sensing material based on the analyte gas of interest to be sensed by the sensor. The one or more processors are configured to select one or more responses from the sensor that provide one or more of rejection of one or more interfering gases, resolution between at least two gases, improved low detection range of the one or analyte gases, improved high detection range of the one or more analyte gases, improved response linearity of the one or more of the analyte gases, improved dynamic range of measurements of the one or more of the analyte gases, or one or more combinations thereof as compared to non-selected responses from the sensor.

In one embodiment, a method includes receiving with one or more processors an electrical signal from an impedance gas sensor that is in contact with a sample having one or more analyte gases therein. The impedance sensor including electrodes and a sensing region circuit having a sensing material that receives electrical stimuli at one or more different frequencies from the electrodes. A frequency of the one or more different frequencies at which the electrodes of the sensor apply the electrical stimuli to the sensing material is based on an analyte gas of interest to be sensed by the sensor of the one or more analyte gases. The method includes determining a concentration of the analyte gas of interest of the one or more analyte gases in the sample based on the electrical signal received from the sensor. The electrical signal is representative of an impedance of the sensing material during exposure of the sensing material to the sample at one or more different frequencies. The impedance of the sensing material indicates a concentration of the analyte gas of interest in the sample.

In one embodiment, a system includes an impedance gas sensor configured to be in contact with a sample having one or more analyte gases therein. The impedance sensor includes a sensing material that receives electrical stimuli at one or more frequencies. The system includes one or more processors configured to receive at electrical signal from the sensor that is representative of an impedance of the sensing material during exposure of the sensing material to the sample at the one or more different frequencies. The impedance is representative of a concentration of an analyte gas of interest of the one or more analyte gases in the sample. The one or more processors are configured to change the one or more frequencies at which the electrical stimuli are applied to the sensing material to change a sensitivity of the sensing material to different gases of the one or more analyte gases. The one or more processors are configured to select one or more responses from the sensor that provide one or more of rejection of one or more interfering gases, resolution between at least two gases, improved low detection range of the one or more analyte gases, improved high detection range of the one or more analyte gases, improved response linearity of the one or more analyte gases, improved dynamic range of measurements of the one or more analyte gases, or one or more combinations thereof as compared to non-selected responses from the sensor.

BRIEF DESCRIPTION OF THE DRAWINGS

FIG. 22B illustrates a graphical illustration of a calculated impedance response of the sensor of FIG. 22A in accordance with one embodiment;

DETAILED DESCRIPTION

Figure 1:
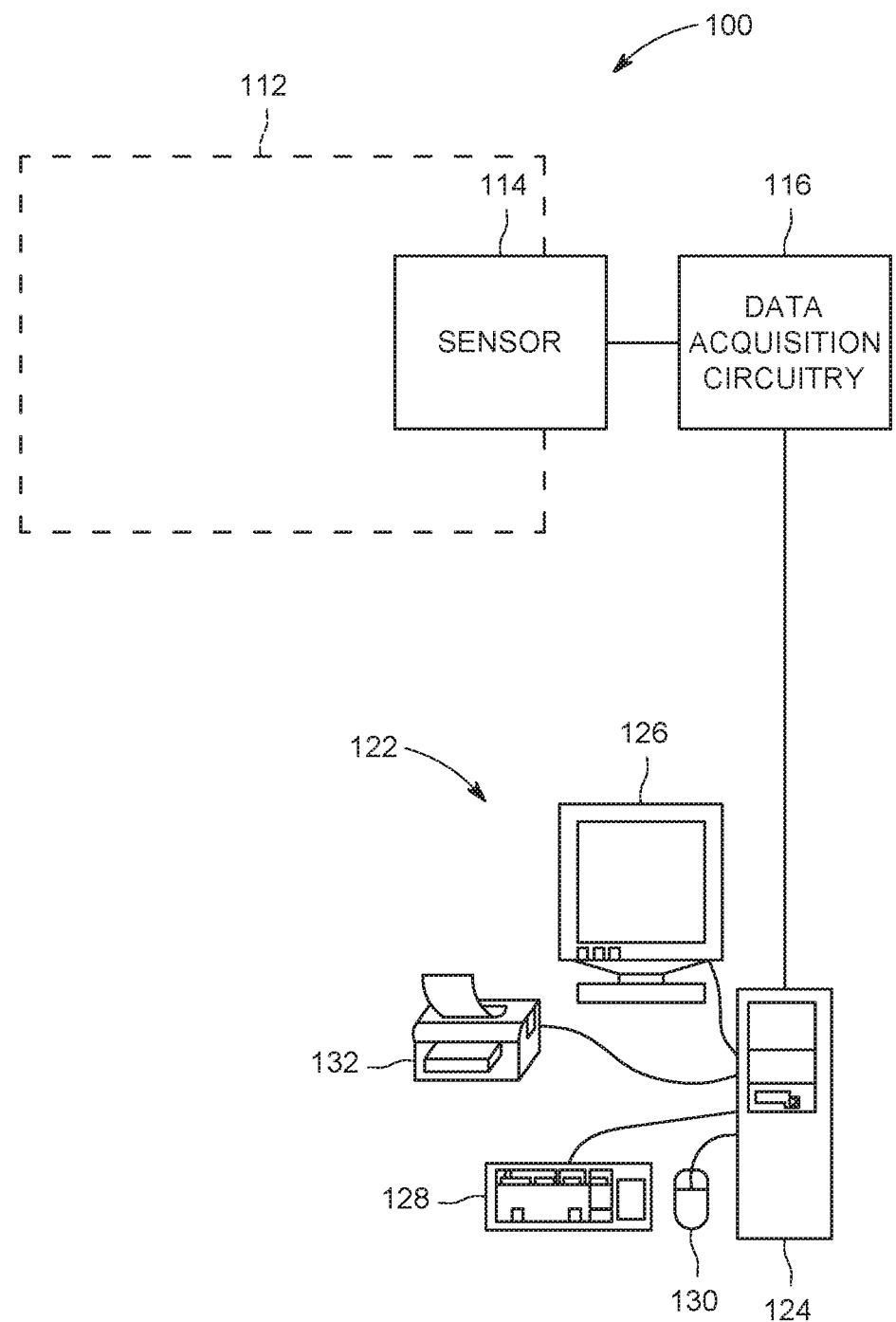
FIG. 1 illustrates one embodiment of a sensing system in accordance with one embodiment.

One or more embodiments of the inventive subject matter described herein provide for sensing systems and methods that perform sensor operations with controlled sensor response selectivity and sensitivity at different sensitivity ranges of analyte detection upon exposure to different gases. Response selectivity is representative of the ability to distinguish between different gases using a single sensor, through appropriate choice of frequency scan and/or analysis. These sensing systems and methods can sense and differentiate between different analyte gases in an insulating transformer oil or in ambient air. Also, the sensing systems and methods present a gas sensor operation with controlled sensor response linearity. Response linearity is representative of multivariable analysis that can provide (at certain frequencies) increased linearity of detection of a gas sensor, leading to simpler calibration and improved measurement range. For example, the sensor calibration may refer to a relationship between an analyte gas concentration and a sensor response signal used to determine performance characteristics of the sensor, such as linearity, a dynamic range, response linearity, low detection range, high detection range, and the like. Sensor response linearity of an analyte gas (e.g., an analyte gas of interest) can include a deviation of an experimentally determined calibration line from an ideal straight target line. Additionally, the sensor dynamic range of measurements of an analyte gas may be an analyte gas concentration range between and including the lowest concentration of the analyte gas and the highest concentration of the analyte gas that may be quantifiable by the sensor.

An insulating oil of an oil-fitted transformer is employed to insulate and suppress corona and arcing and to serve as a coolant. However, the insulating oil gradually deteriorates under the impact of electrical, thermal and environmental stresses during the life of the transformer. Different types of gases are generated in the insulating oil depending on the deterioration process. Examples of these gases include hydrogen, carbon monoxide, carbon dioxide, methane, ethane, ethylene, and acetylene. For example, thermal decomposition of mineral oil produces hydrogen and methane. Thermal decomposition of cellulose and other solid insulating materials produces carbon monoxide, carbon dioxide, and water vapor. Such gases are detected and monitored in real time using multivariable sensors as described in more detail below.

In one or more embodiments of the inventive subject matter described herein, the sensing material is a metal oxide, however the accepted limitations of current sensors are non-linear responses that follow the power law and non-selective responses to different gases. These limitations originate from the conventional resistance measurements of metal oxide (MOX) sensors. One or more embodiments of the inventive subject matter described herein unexpectedly found a frequency dependence of such sensor on its selectivity, response linearity to an analyte gas, improved low detection range of analyte gases, improved high detection range of analyte gases, improved dynamic range of measurements of analyte gases as compared to conventional resistance response from the sensor.

These sensing systems and methods provide a low cost, highly selective sensing method and system with simplified or eliminated gas extraction. Relevant features of multivariable sensing include linearity, selectivity, and upper range extension, sensitivity/detection limit improvements. The upper range extension is representative of, through appropriate choice of frequency scan, a sensor acquisition capability that can be extended outside the conventional range that can be obtained with known resistance methods. This can add significant benefits on gassing transformers and on load tap changing mechanisms. Through frequency scanning or frequency selection, the sensor systems and methods may unlock improved low detection limit (LDL) capability, overcoming signal/noise limitations on conventional resistance analysis, leading to lower detection limits than conventionally obtained through known resistance methods. For example, the sensor low detection limit (LDL) may refer to the lowest quantity (e.g., concentration) of an analyte gas that is distinguishable by the sensor from an absence of the analyte gas with a designated confidence limit, such as three standard deviations of the sensor response signal when exposed to a clean sample without an analyte gas and with few interferences. The sensor LDL may also be referred to as a detection limit, a lower limit of detection, a limit of detection, or the like. Alternatively, a sensor high detection limit may refer to the highest quantity (e.g., concentration) of an analyte gas that may be distinguishable by the sensor from a smaller analyte gas quantity within a designated confidence limit, such as three standard deviations of the sensor response signal when exposed to the highest quantity (e.g., concentration) of the analyte gas.

At least one technical effect of the various embodiments herein can selectively measure amounts or concentrations of one or more hydrocarbons using a single sensor system or sensor in order to detect a potentially catastrophic failure. For example, the systems and methods may sense the presence and/or amount of carbon monoxide CO, carbon dioxide $CO_2$, hydrogen $H_2$, methane $CH_4$, acetylene $C_2H_2$, ethylene $C_2H_4$, ethane $C_2H_6$, and other gases in transformer oil. The sensed amount of analyte gas may indicate a potential catastrophic failure of the powered system or another abnormal system condition. As an additional technical effect, these sensing systems and methods unexpectedly found a frequency dependency of selectivity and linearity of sensors based on semiconductor metal oxides.

FIG. 1 illustrates one embodiment of a sensing system 100. The system 100 examines a fluid in contact with the system 100. The fluid has one or more analyte gases therein. This fluid may be transformer oil or any insulating fluid of an electrical transformer that is installed and/or disposed of below a ground level, above the ground level, near to the ground level, or any other position. Another example of the fluid is ambient air. Another example of the fluid is ambient air with relatively small concentrations of analyte gases.

The system 100 may include a fluid reservoir 112 for holding the fluid and one multivariable gas sensor 114 at least partially disposed in, on, or within the fluid reservoir 112. Alternatively, the sensor 114 may be set in a flow path of the fluid outside of the reservoir 112, such as coupled to in-line connectors in fluid communication with the fluid reservoir that define a flow path. In one embodiment, the sensor 114 may provide continuous monitoring of the fluid within the reservoir or flow path. In one or more embodiments, the sensor 114 may be an impedance gas sensor, a photonic sensor, an electronic sensor, a hybrid sensor, or another type of sensor. Optionally, the multivariable gas sensor may be a sensor array.

The sensor 114 may detect characteristics or properties of the fluid via a resonant or non-resonant impedance spectral response. One or more of the inductor-capacitor-resistor resonant circuits (LCR resonators) may measure the resonant impedance spectral response of the sensor. A non-resonant impedance spectral response is measured when the circuit does not contain an inductor. The resonant or non-resonant impedance spectrum of the sensor 114 in proximity to the fluid varies based on sample composition and/or components and/or temperature. The measured resonant or non-resonant impedance values Z' (which may be the real part of resonant impedance, Zre) and Z" (which may be the imaginary part of resonant impedance, Zim) reflect the response of the sensor 114 to the fluid.

Other embodiments of the inventive subject matter described herein include other designs of sensors besides resonant and non-resonant impedance sensors. Other sensors can be capacitor sensors, electro-mechanical resonator sensors (e.g., tuning forks, cantilever sensors, acoustic device sensors), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors. The sensor may generate electrical or optical stimuli in response to measured gas in transformer oil or in isolating fluid. The insulating fluid of an electrical transformer may be insulating oil, mineral oil, synthetic oil, vegetable oil, and any other appropriate insulating fluid.

An electrical field may be applied to a sensing material or sensing film of the sensor 114 via electrodes. The distance between the electrodes and the electrodes geometry as well as the applied periodic voltage to the electrodes, may define the magnitude of the electric field applied to the sensor 114 (e.g., to the sensing material or film). The electrodes may be in direct contact with the sensing material. For example, the sensor 114 may be a combination of a sensing region and associated circuits and/or the sensing region may be coated with the sensing material. The sensing material may be semiconductor material or metal oxide material.

Suitable sensors may include single use or multi-use sensors. A suitable multi-use sensor may be a re-usable sensor that may be used during the lifetime of a system in which it may be incorporated into. In one embodiment, the sensor may be a single use sensor that may be used during all or part of a reaction or process.

Data from the sensor 114 may be acquired via data acquisition circuitry 116, which may be associated with the sensor or which may be associated with a control system, such as a controller or workstation 122 including data processing circuitry, where additional processing and analysis may be performed. The controller or workstation 122 may include one or more wireless or wired components, and may also communicate with the other components of the system 100. Suitable communication models include wireless or wired. At least one suitable wireless model includes radio frequency devices, such as radio frequency identification (RFID) wireless communications. Other wireless communication modalities may be used based on application specific parameters. Nonlimiting examples include Bluetooth, Wi-Fi, 3G, 4G, 5G, and others. For example, where there may be electromagnetic field (EMF) interference, certain modalities may work where others may not. The data acquisition circuitry 116 optionally can be disposed within the sensor 114. Other suitable locations may include disposition being within the workstation 122. Further, the workstation 122 can be replaced with a control system of the whole process where the sensor and its data acquisition circuitry may be connected to the control system of process.

The data acquisition circuitry 116 may be in the form of a sensor reader, which may be configured to communicate wirelessly or wired with the fluid reservoir 112 and/or the workstation 122. For example, the sensor reader may be a battery-operated device and/or may be powered using energy available from the main control system or by using harvesting of energy from ambient sources (light, vibration, heat, or electromagnetic energy). The data acquisition circuitry is an impedance analyzer that may provide scanning capability to measure sensor impedance across a predetermined frequency range, for example from 0.001 Hz to 10 GHz, from 0.1 Hz to 1 GHz, from 1 Hz to 100 MHZ, from 10 Hz to 10 MHz, or from 1000 Hz to 100 kHz. An impedance analyzer may provide capability to measure sensor impedance at discrete predetermined frequencies, for example at 1 Hz, 10 Hz, 100 Hz, 1 kHz, 10 kHz, 100 kHz, 1 MHz, 10 MHz, or 100 MHz.

Additionally, the data acquisition circuitry may receive data from one or more sensors 114 (e.g., multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. The sensors 114 may be positioned on or in oil fluid reservoirs, associated piping components, connectors, flow-through components, and any other relevant process components. The data acquisition circuitry 116 may include one or more processors for analyzing the data received from the sensor 114. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

In addition to displaying the data, the operator workstation 122 may control the above-described operations and functions of the system 100. The operator workstation 122 may include one or more processor-based components, such as general purpose or application-specific computers or processors 124. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation 122 or by associated components of the system 100. Alternatively, the programs and routines may be stored on a computer accessible storage and/or memory remote from the operator workstation 122 but accessible by network and/or communication interfaces present on the computer 124. The computer 124 may also comprise various input/output (I/O) interfaces, as well as various network or communication interfaces. The various I/O interfaces may allow communication with user interface devices, such as a display 126, keyboard 128, electronic mouse 130, and printer 132, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

Figure 2:
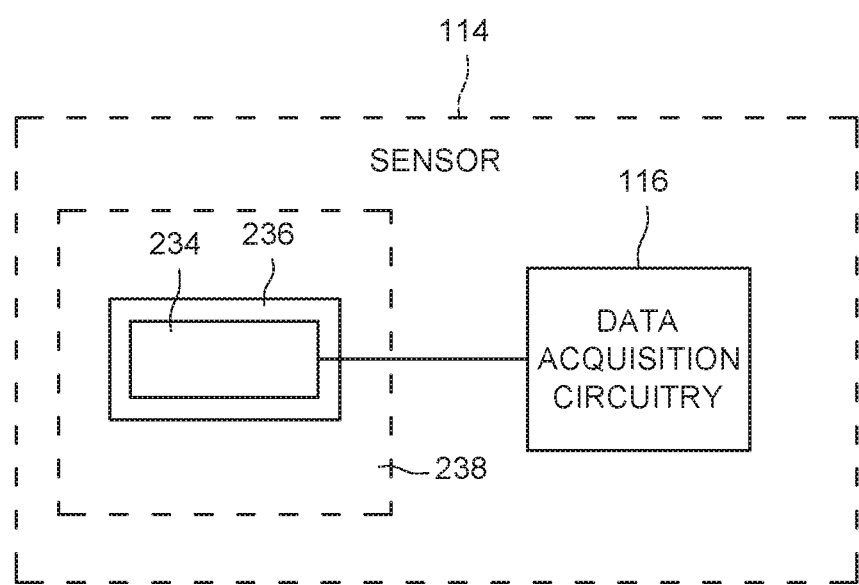
FIG. 2 illustrates a non-limiting example of a design of a sensor shown in FIG. 1 in accordance with one embodiment.

FIG. 2 illustrates a non-limiting example of a design of the sensor 114. A sensing electrode structure 234 of the sensor 114 may be connected to the data acquisition circuitry 116. The sensing electrode structure 234 can be coated with a sensing film 236. The sensing electrode structure 234, with the sensing film 236, forms a sensing region circuit 238. The sensing electrode structure 234, with the sensing film 236 that forms the sensing region circuit 238, may operationally contact a fluid. The fluid contains the one or more analyte gases therein.

Suitable interdigital electrode structures for probing a fluid sample include two- and four-electrode structures. Suitable materials for electrodes include stainless steel, platinum, gold, noble metals, and others. Suitable materials of a substrate may include silicon dioxide, silicon nitride, alumina, ceramics, and others. Suitable examples of sensing materials or sensing films include a metal oxide material, a composite material, semiconducting materials, n-type semiconducting materials, p-type semiconducting materials, nanocomposite materials, inorganic materials, organic materials, polymeric materials, formulated materials, or the like. Suitable electrodes may be formed using metal etching, screen-printing, ink-jet-printing, and mask-based metal deposition techniques. The thickness of fabricated electrodes on the substrates may be in the range from about 10 nanometers to about 1000 micrometers. The materials for the interdigital electrode structures, substrate, sensing layer, and electrode formation methods may be selected based at least in part on the application specific parameters.

Figure 3:
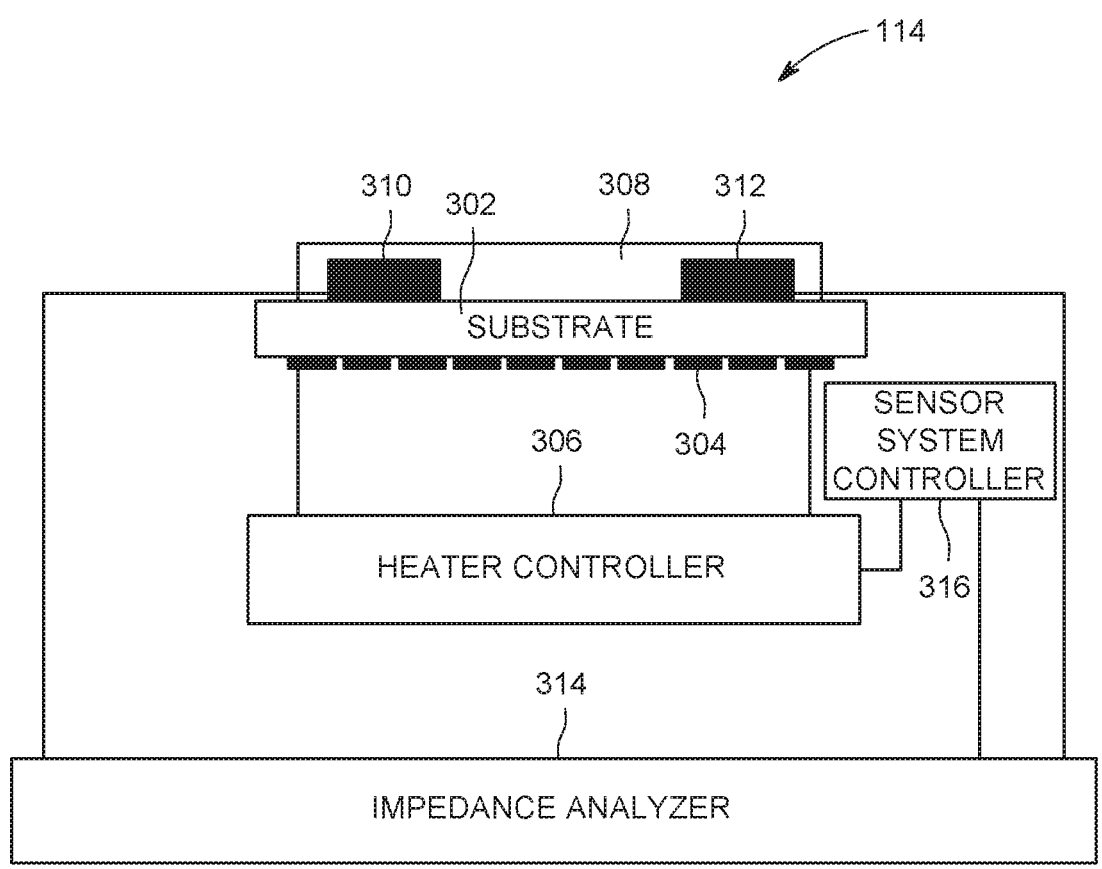
FIG. 3 illustrates one embodiment of a sensor in accordance with one embodiment.

FIG. 3 illustrates one embodiment of the multivariable gas sensor 114. The sensor 114 may represent another version of the sensors or sensing systems described herein. The sensor 114 includes a substrate 302, such as a dielectric material. One or several heating elements 304, such as high resistance bodies, are coupled to one side of the substrate 302. The heating elements 304 receive electric current from a heater controller 306, which represents hardware circuitry that conducts the heater current or voltage to the heating elements 304 to heat the substrate 302 and to heat a sensing material or sensing film 308 that is coupled to the other side of the substrate 302 and to electrodes 310 and 312. For example, in one or more embodiments of the inventive subject matter described herein, the sensing material utilizes a metal oxide sensing film. The sensing material 308 can include one or more materials deposited onto the substrate 302 to perform a function of predictably and reproducibly affecting the impedance sensor response upon interaction with the environment. For example, a metal oxide such as SnO2 may be deposited as the sensing material 308.

Sensing electrodes 310, 312 are coupled with or disposed in the sensing material 308 and are connected with the substrate 302 in the illustrated embodiment. The sensing electrodes 310, 312 are conductive bodies that are conductively coupled with an impedance analyzer circuit 314 having one or more processors that include one or more microprocessors, field programmable gate arrays, and/or integrated circuits. In one or more embodiments, the sensing electrodes 310, 312 may be coated with a sensing material that is responsive to one or more analyte gases of interest. The one or more processors of the impedance analyzer circuit 314 receives an electrical signal from the sensor 114 that represents the impedance of the sensing material 308 during exposure of the sensing material 308 to the fluid sample. The impedance analyzer circuit 314 examine the impedance response of the sensing material 308 in order to determine the presence and/or amount (e.g., concentration) of one or more analyte gases in the environment to which the sensing material 308 is exposed, as described herein.

The impedance analyzer circuit 314 may provide scanning capability to measure sensor impedance across a predetermined frequency range. Alternatively, impedance analyzer circuit 314 may provide capability to measure sensor impedance at discrete determined frequencies or at a single frequency. A sensor system controller 316 directs the impedance analyzer circuit 314 on what frequencies or a frequency to apply for interrogation of the sensing material or sensing film 308 and what integration time to apply to measure the sensor response at each frequency. Also, sensor system controller 316 directs heater controller 306 on what voltage or power to apply to heating elements 304 or to what temperature to bring the heating elements 304. In one or more embodiments, the multivariable gas sensor 114 operates at a temperature of at least 50° above an ambient temperature. Optionally, the sensor 114 may operate at a temperature greater than and/or less than 50° above and/or below the ambient temperature.

In one embodiment, the system may measure an impedance (f) (represented by Eq. (1)) of exposure of the sensing material or sensing film of the sensor to a fluid sample while the sensing material or sensing film is excited with electric stimuli and heated:

$$(f) = Z_{re}(f) + jZ_{im}(f) \qquad \text{Eq. (1)}$$

where $Z_{re}(f)$ may be the real part of the impedance and $Z_{im}(f)$ may be an imaginary part of the impedance. In one embodiment, the real part of the impedance $Z_{re}(f)$ and imaginary part of the impedance $Z_{im}(f)$ may be two components of a non-resonant impedance (f). In one embodiment, the real part of the impedance $Z_{re}(f)$ and imaginary part of the impedance $Z_{im}(f)$ may be two components of a resonant impedance (f).

In some embodiments, the non-resonant impedance sensor response may be measured at multiple frequencies across a predetermined frequency range, for example from 0.001 Hz to 10 GHz, from 0.1 Hz to 1 GHz, from 1 Hz to 100 MHz, from 10 Hz to 10 MHz, or from 1000 Hz to 100 kHz. This non-resonant impedance sensor response may be analyzed by multivariate analysis.

In one embodiment, the resonant impedance spectral response of the sensor may be a multivariable resonant response as more than one frequency may be utilized to measure sensor response across the resonance of the sensor. In some embodiments, the resonant impedance response of the sensor may be a multivariable resonant response because more than one frequency may be utilized to measure sensor response outside the resonance peak of the sensor. In some embodiments, the sensor response may be measured at multiple frequencies across the resonance of the sensor. For example, if the sensor with the electrodes coated with the sensing film resonates at about 10 MHz, the measured frequencies and associated sensor responses may be measured from about 8 MHz to about 12 MHz. This resonant impedance sensor response may be analyzed by multivariate analysis.

One or more embodiments of the sensor system described herein can incorporate the sensor 114, where the sensor 114 is connected to the impedance analyzer circuit 314. The impedance analyzer circuit 314 measures the response of the sensor to different gases, where the range of frequencies for gas analysis is selected to be at frequencies around the inflection point of the imaginary part of the impedance spectrum of the sensor. The inflection point of the imaginary part of the impedance spectrum is also known as the relaxation peak or the relaxation point of the relaxation region of the imaginary part of the impedance spectrum of the sensing material. In one or more embodiments described herein, the impedance analyzer circuit 314 selects one or more responses of the multiple responses from the sensor 114 that provide rejection of one or more interfering gas, resolution between at least two analyte gases, an improved sensor response selectivity, improved response linearity to analyte gases, improved low detection range of analyte gases, improved high detection range of analyte gases, improved dynamic range of measurements of analyte gases, or one or more combinations thereof over the conventional non-selected and/or resistance measurements of the sensor and where the sensor includes the one or more sensing materials 308. The sensing materials 308 may be one or more of dielectric polymers, conducting polymers, metal oxides, catalytic metals, macrocycles, cage compounds, carbon allotropes, ionic liquids, composite materials, semiconducting nanowires, functionalized metal nanoparticles, or the like.

Figure 4:
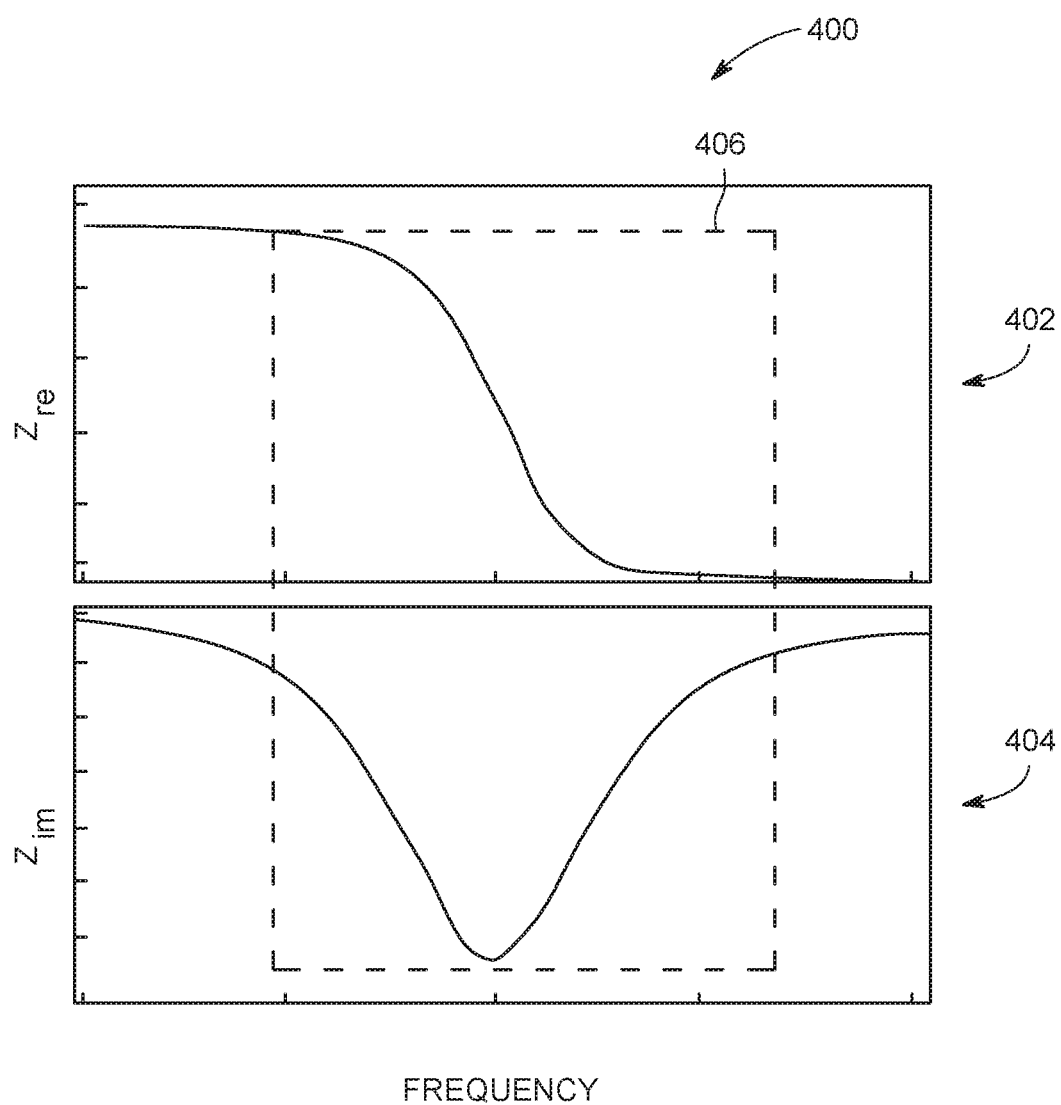
FIG. 4 illustrates a graphical illustration of measured responses corresponding to a real and imaginary impedance responses of a sensor described herein in accordance with one embodiment.

FIG. 4 illustrates a graphical illustration of measured responses 400 corresponding to a real and imaginary impedance responses 402, 404 of the sensors described herein in accordance with one embodiment. For example, the impedance response 400 can represent the impedance sensor response of the sensor 114 configured as a non-resonant sensor based on a stimulation waveform generated by the circuitry 116. The impedance responses 400 are measured by the circuitry 116 based on a measurement signal. For example, the circuitry 116 may receive the measurement signal from the electrodes 310, 312 in contact with the sensing material 308. The measurement signal is an electrical signal generated by the sensing material 308 in response to the stimulation waveform and the ambient environment to which the sensing material 308 is exposed. The measurement signal is representative of the impedance response of the sensing material 308. For example, the measurement signal may have electrical characteristics (e.g., voltage, current, frequency, and/or the like), which may be utilized by the circuitry 116 to calculate the impedance responses 400. The impedance responses 400 are divided into real portions 402 corresponding to the real impedance, Zre(f) of the impedance responses 400, and imaginary portions 404 of an imaginary impedance, Zim(f).

Impedance measurements of the real portions 402 corresponding to the real impedance Zre(f) of the impedance responses 400, and imaginary portions 404 of the imaginary impedance Zim(f) are performed at frequencies around the inflection point of the imaginary portion 404. For example, the impedance measurements are taken within a spectral range 406 that provides control of the sensor response selectivity, response linearity, improved low detection range, improved high detection range, improved dynamic range of measurements as compared to resistance response from the same sensor upon exposure to different analyte gases.

The electrodes 310, 312 apply electrical stimuli to the sensing material 308 at one or more different frequencies in and around the spectral range 406. The spectral range 406 may represent several frequencies such as less than 1,000 Hz, between and including 1,000 Hz and 100,000 Hz, greater than 100,000 Hz, or the like. For example, in one embodiment, the sensing system 100 includes a sensor 114, where the sensor 114 is connected to an impedance analyzer circuit 314, where the impedance analyzer circuit 314 measures the response of the sensor 114 to different analyte gases, where the range of frequencies for gas analysis is selected to be at frequencies around the inflection point of the imaginary part of the impedance spectrum of the sensor and where the impedance analyzer circuit selects one or more responses of the multiple responses from the multivariable sensor that provides rejection of one or more interfering gas, resolution between at least two analyte gases, an improved sensor response selectivity, improved response linearity of the analyte gas, improved low detection range of the analyte gas, improved high detection range of the analyte gas, improved dynamic range of measurements of the analyte gas as compared to resistance response from the same sensor upon exposure to different analyte gases, or one or more combinations thereof compared to non-selected responses from the sensor 114.

One or more embodiments of the sensors and the sensor system described herein can be used to measure a gas mixture dissolved in oil and extracted from oil similar to common transformer dissolved gas analysis (DGA) methods. The sensor and the sensor system incorporate a sensing element, where the sensing element is connected to the impedance analyzer circuit, where the impedance analyzer circuit measures the response of the sensing element when exposed to a gas mixture present in oil and maybe that has been extracted from oil. For example, FIGS. 5-8 illustrate a non-limiting example of the sensor 114 performing an exemplary gas analysis. In the present example, the analyte gas of interest of the fluid may be hydrogen gas (H2). Optionally, the analyte gas of interest may be CO, CO2, CH4, CH4, C2H2, C2H4, C2H6, or the like. Additionally or alternatively, the analyte gas may include one or more fault gases that are used for transformer diagnostics. The sensor 114 changes the frequency at which the electrical stimuli are applied to the sensing material 308 by means of the electrodes 310, 312 in order to receive an electrical signal from the sensor 114 that is representative of the impedance of the sensing material representing a concentration of the H2 analyte gas of interest. FIGS. 5-8 will be discussed in detail together.

Figure 5:
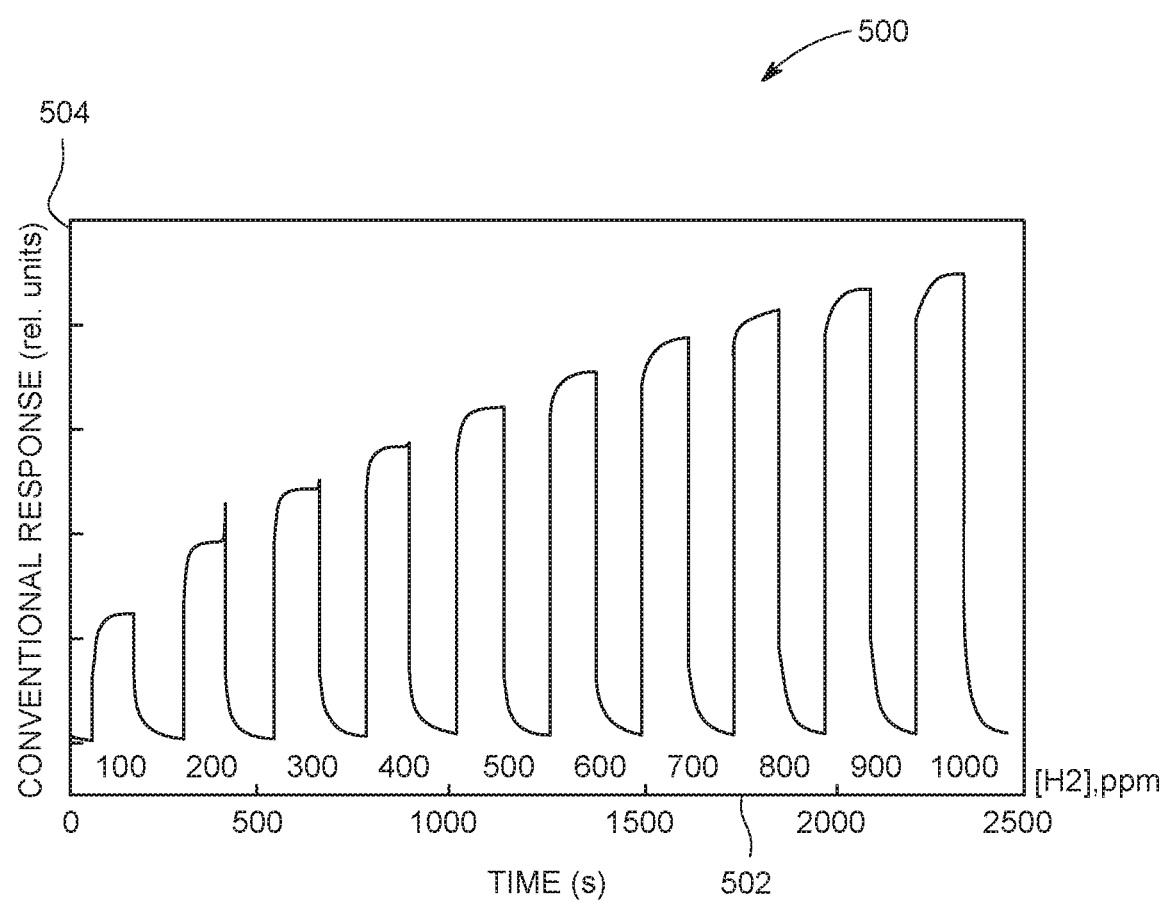
FIG. 5 illustrates a graphical illustration of measured resistance responses of a conventional sensor in accordance with one embodiment.

FIG. 5 illustrates a conventional resistance response 500 of the sensor 114 to changes in H2 concentrations ranging from 0 parts per million (ppm) to 1000 ppm in steps of 100 ppm. For example, FIG. 5 illustrates a conventional non-linear resistance response 500 to a resistive sensor exposed to a sample containing H2. The resistance response 500 is shown alongside a horizontal axis 502 representative of time and a vertical axis 504 representative of magnitudes of the sensor response. For example, the vertical axis 504 may represent resistances of the sensor. The response 500 represents the resistance measured by the sensor for hydrogen gas (e.g., the analyte gas of interest).

Figure 6:
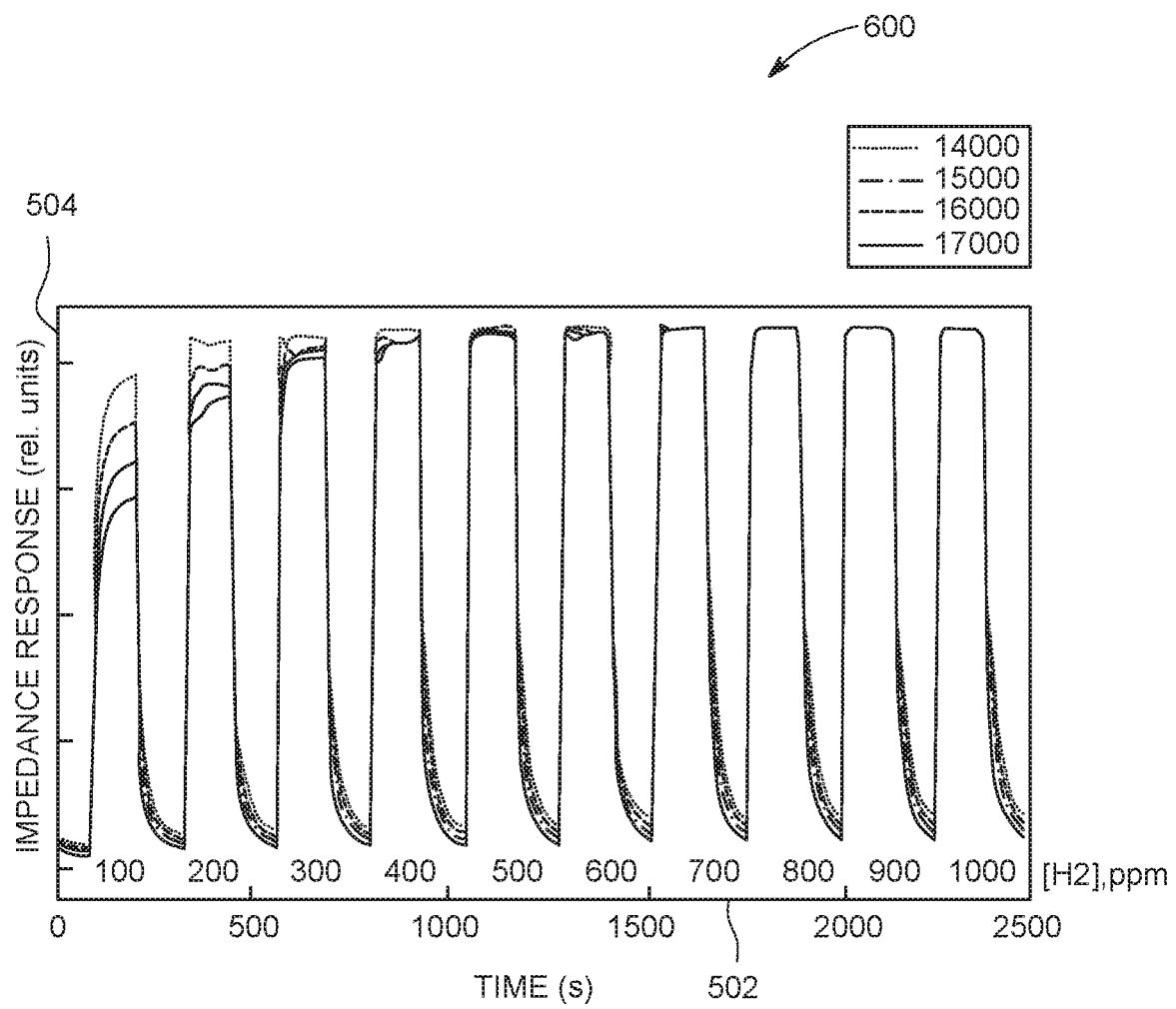
FIG. 6 illustrates a graphical illustration of measured resistance responses of a sensor having a first excitation and measurement condition in accordance with one embodiment.

FIG. 6 illustrates impedance response Zre 600 of the sensor 114 to the same step changes in H2 concentrations of FIG. 5, ranging from 0 ppm to 1000 ppm in steps of 100 ppm, having a first excitation and measurement condition.

The first excitation and measurement condition includes performing excitation and measurement of the gas response of the sensing material 308 at frequencies 14,000 Hz, 15,000 Hz, 16,000 Hz, and 17,000 Hz. Optionally, more than four or less than four different frequencies at greater than or less than 1,000 Hz intervals may be used to apply electrical stimuli to the sensing material 308. For example, the impedance analyzer 314 selects a frequency, a frequency range, or the like, of the one or more different frequencies at which the electrodes 310, 312 are to apply the electrical stimuli to the sensing material 308 based on the analyte gas of interest (e.g., $H_2$) that is to be sensed by the sensor 114. The impedance response 600 is shown alongside the horizontal axis 502 representative of time and the vertical axis 504 representative of magnitudes of the sensor impedance response. Under the first excitation and measurement condition, the sensor 114 demonstrates an enhanced sensitivity to the presence of H2 at low concentration levels of H2. For example, the sensor 114 demonstrates an enhanced sensitivity to H2 gas between, or substantially between, concentration levels of 0 ppm and 500 ppm when the low frequency electrical stimuli of the first excitation and measurement condition are applied to the sensing material 308 as compared to the resistance response of the same sensing material as shown in FIG. 5. The enhanced sensitivity to the presence of H2 at low concentration levels of H2 with the same level of sensor noise indicates the improved sensor low detection range of H2.

Figure 7:
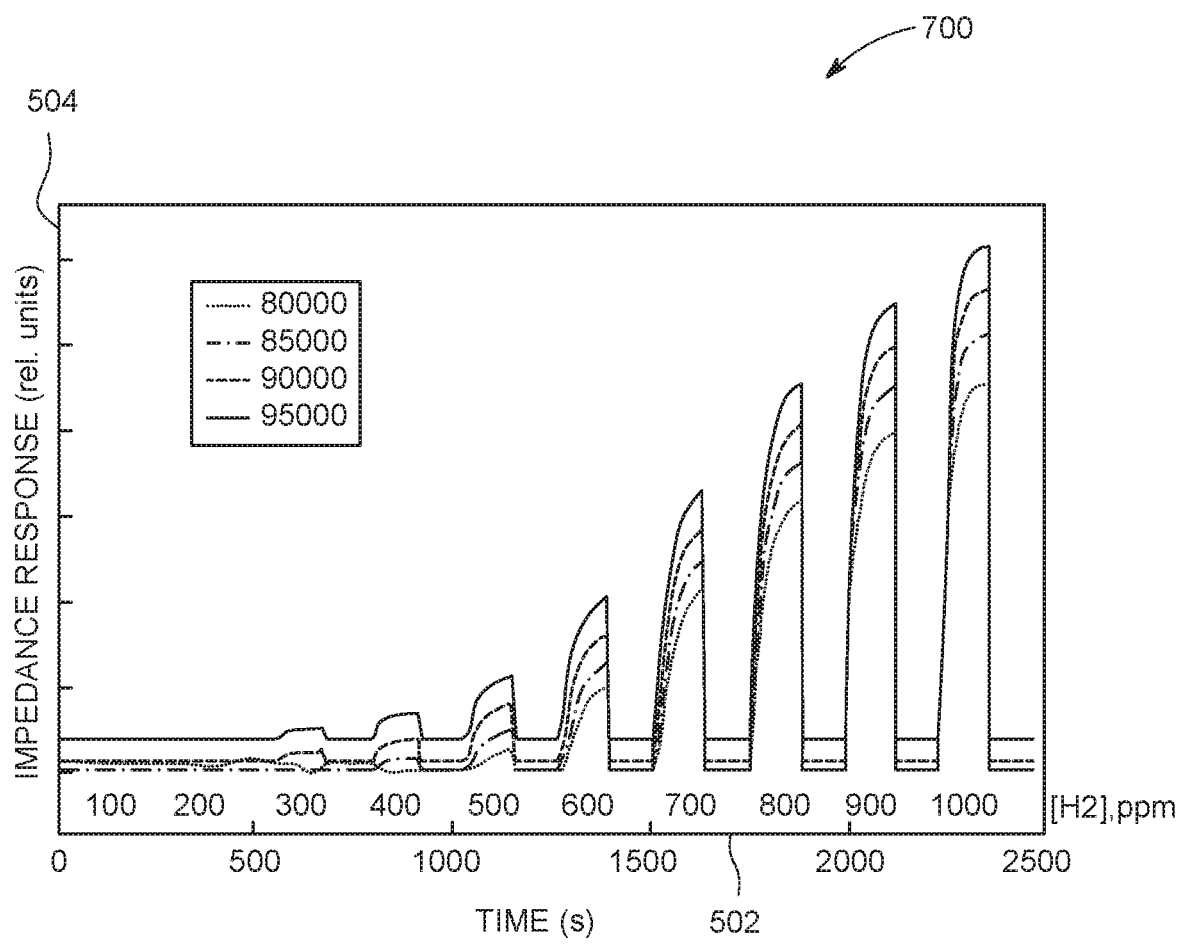
FIG. 7 illustrates a graphical illustration of measured resistance responses of a sensor having a second excitation and measurement condition in accordance with one embodiment.

FIG. 7 illustrates impedance response Zre 700 of the sensor 114 to the same step changes in H2 concentrations of FIG. 5, ranging from 0 ppm to 1000 ppm in steps of 100 ppm, having a second excitation and measurement condition. The second excitation and measurement condition includes performing excitation and measurement of the gas response of the sensing material 308 at frequencies 80,000 Hz, 85,000 Hz, 90,000 Hz, and 95,000 Hz. Optionally, more than four or less than four different frequencies at greater than or less than 1,000 Hz intervals may be used to apply electrical stimuli to the sensing material 308. The impedance response 700 is shown alongside the horizontal axis 502 representative of time and the vertical axis 504 representative of magnitudes of the sensor impedance response. Under the second excitation and measurement condition, the sensor 114 demonstrates an enhanced sensitivity to the presence of H2 at high concentration levels of H2. For example, the sensor 114 demonstrates an enhanced sensitivity to H2 gas between, or substantially between, concentration levels of 500 ppm and 1,000 ppm when the high frequency electrical stimuli of the second excitation conditions are applied to the sensing material 308 as compared to the resistance response of the same sensing material as shown in FIG. 5. The enhanced sensitivity to the presence of H2 at high concentration levels of H2 with the same level of sensor noise also indicates the improved sensor high detection range of H2.

Figure 8:
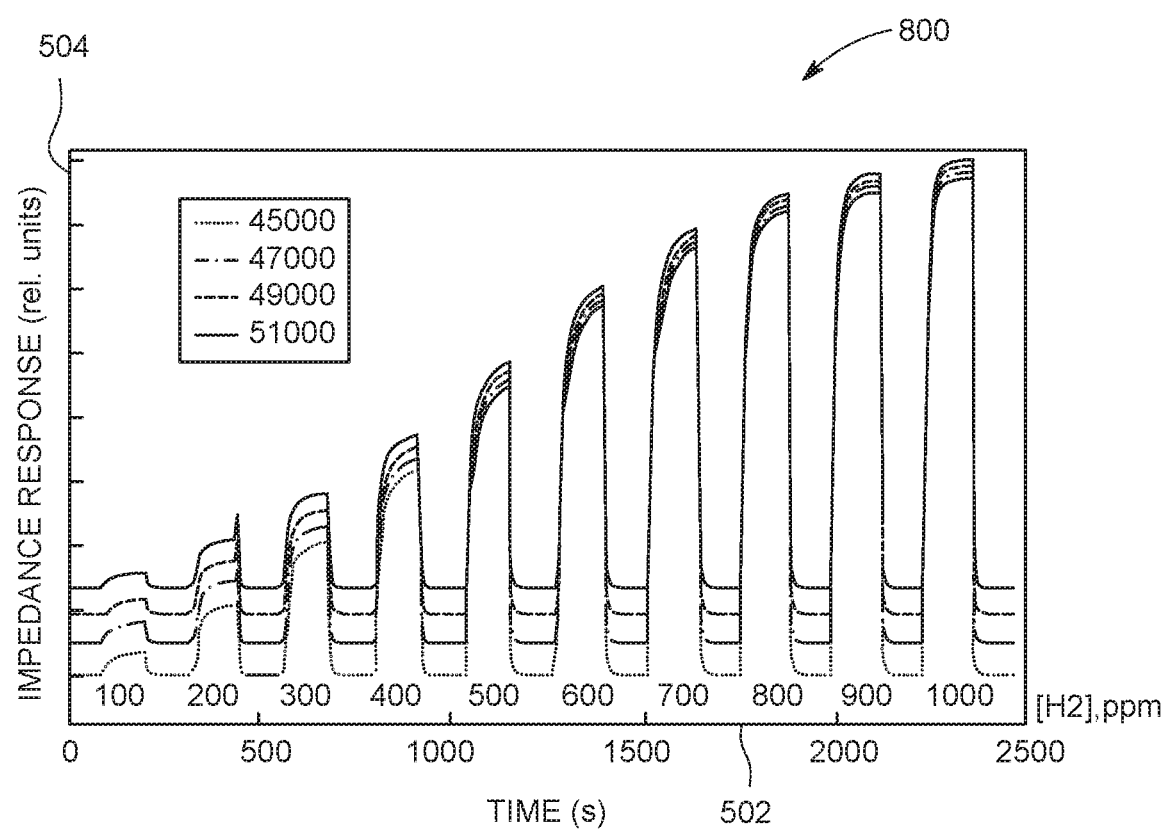
FIG. 8 illustrates a graphical illustration of measured resistance responses of a sensor having a third excitation and measurement condition in accordance with one embodiment.

FIG. 8 illustrates impedance response Zim 800 of the sensor 114 to the same step changes in H2 concentrations of FIG. 5, ranging from 0 ppm to 1000 ppm in steps of 100 ppm, having a third excitation and measurement condition. The third excitation and measurement condition includes performing excitation and measurement of the gas response of the sensing material 308 at frequencies 45,000 Hz, 47,000 Hz, 49,000 Hz, and 51,000 Hz. Optionally, more than four or less than four different frequencies at greater than or less than 1,000 Hz intervals may be used to apply electrical stimuli to the sensing material 308. The impedance response 800 is shown alongside the horizontal axis 502 representative of time and the vertical axis 504 representative of magnitudes of the sensor impedance response. Under the third excitation and measurement condition, the sensor 114 demonstrates an enhanced sensitivity to the presence of H2 at the moderate concentration levels of H2 as compared to the resistance response of the same sensing material as shown in FIG. 5.

The Zre and Zim impedance responses 600, 700, 800 of the sensing material 308 represent enhanced sensitivity at varying concentration levels of H2 at the different frequencies. The sensitivity of the sensing material changes based on which of the different frequencies is used to apply the electric stimuli. For example, the system 100 is configured to improve a low detection range of the sensor 114 by changing the frequency at which the electrodes 310, 312 apply the electrical stimuli to the sensing material 308.

At the lower frequency range (e.g., the first excitation and measurement condition of FIG. 6), the sensor 114 has an increased sensitivity to the low concentration levels of H2 compared to the moderate or high concentration levels of H2. For example, the sensor 114 may increase a sensitivity of the sensing material 308 to the analyte gas of interest H2 to improve a low detection range of the sensor 114 to at least a detection level of one part per million (1 ppm). Optionally, the sensor may improve a low detection range to a detection level less than 1 ppm. At the higher frequency range (e.g., the second excitation and measurement condition of FIG. 7), the sensor has an increased sensitivity to the high concentration levels of H2 compared to the low or moderate concentration levels of H2. For example, the sensor 114 may increase a sensitivity of the sensing material 308 to the analyte gas of interest H2. At the moderate frequency range (e.g., the third excitation and measurement condition of FIG. 8), the sensor has an increased sensitivity to the moderate concentration levels of H2 compared to the low or high concentration levels of H2.

In contrast to operation of some known sensors, one or more of the sensors described herein may be configured to change the frequency at which the electrodes 310, 312 of the sensor 114 are to apply the electrical stimuli to the sensing material 308 in order to increase a sensitivity of the sensing material 308 to a different analyte gas. For example, the impedance analyzer circuit 314 may apply one or more different frequencies to the sensing material in order to receive an impedance response of the sensing material representative of one or more alternative analyte gases of interest. The impedance responses may represent a concentration of the one or more of the gases CO, CO2, CH4, CH4, C2H2, C2H4, or C2H6. Optionally, the analyte gas may include one or more fault gases to be used for transformer diagnostics. The system 100 provides an improved sensor dynamic measuring range and resolution upon exposure to higher concentrations of gas in contrast to the conventional measurements of some known sensors.

One or more embodiments of the sensor system described herein can be used to test a gas sample that has been extracted from transformer oil, or the like. The sensor 114 is connected to the impedance analyzer circuit 314 that scans the sensing material 308 at different frequencies, where the impedance analyzer circuit 314 provides data output enabling improved sensor selectivity across multiple gases. Sensor selectivity may include the ability of the sensor to respond to an analyte gas of interest and not to respond, or show minimal response, to different analyte gases presented to the sensor either separately (e.g., separate from the analyte gas of interest) or in a mixture with the analyte gas of interest. For example, known sensors may be designed to detect one analyte gas yet may present cross-sensitivity to a second analyte gas. The cross-sensitivity of the first analyte gas with the second analyte gas prohibits known sensors from discriminating between the first and the second analyte gases. For example, fluid samples include plural, different analyte gases therein. The sensing material 308 may be sensitive to different concentrations of the different analyte gases at different respective frequencies of the electrical stimuli applied to the sensing material 308 by the electrodes 310, 312 of the sensor 114.

FIGS. 9-13 illustrate non-limiting examples of the system 100 performing a dissolved gas analysis (DGA) on the fluid sample (e.g., transformer oil) of the fluid reservoir 112 having the one or more analyte gases therein. In the present example, the analyte gas of interest may be hydrogen gas (H2) and the sensor 114 may be an H2 impedance gas sensor. However, conventional metal oxide resistance H2 sensors have a known high cross-sensitivity to C2H2. Thus, these known sensors are unable to discriminate between C2H2 and H2. In the present embodiment, the H2 sensor 114 (e.g., the processors 124) changes the frequency at which the electrical stimuli are applied to the sensing material 308 by means of the electrodes 310, 312 in order to receive an electrical signal from the H2 sensor 114 that is representative of the impedance of the sensing material representing a concentration of the H2 analyte gas of interest. FIGS. 9-13 will be discussed in detail together.

Figure 9:
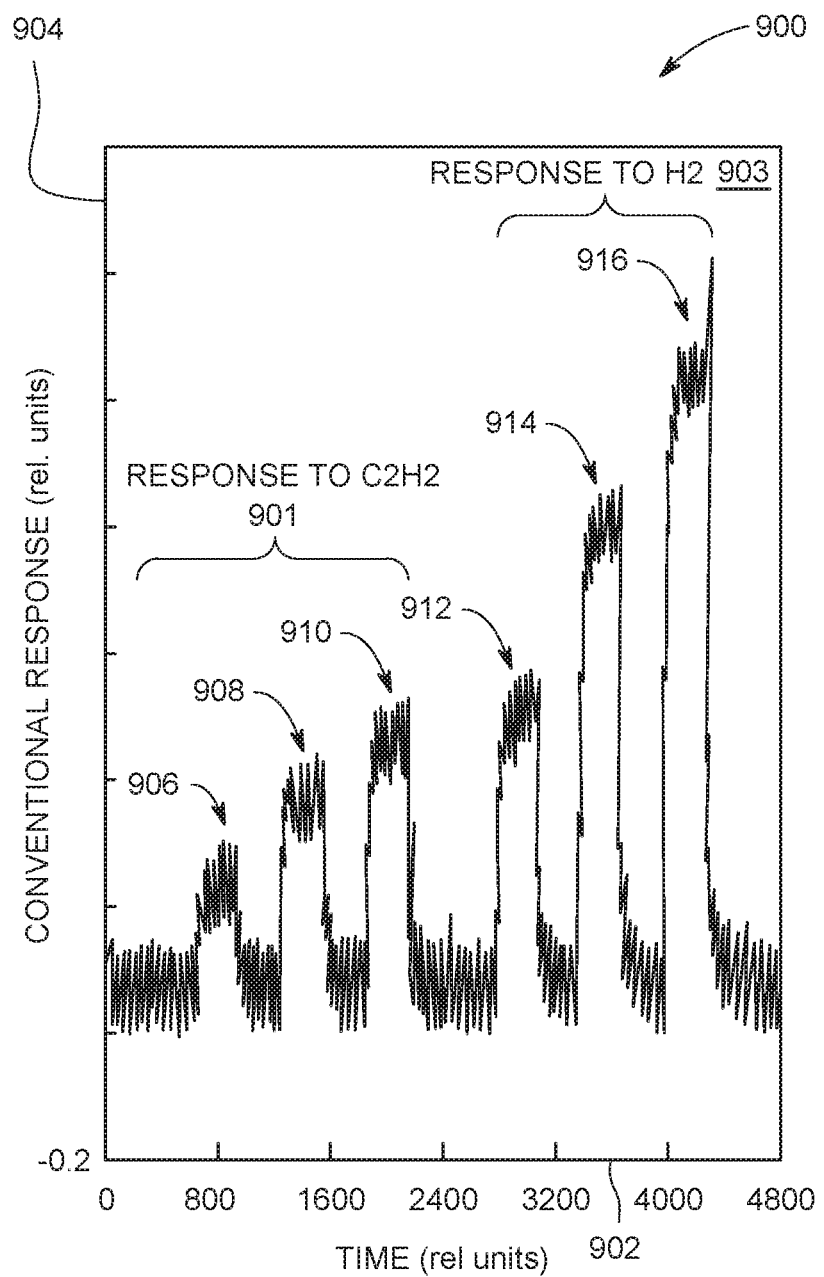
FIG. 9 illustrates a graphical illustration of measured resistance responses of a conventional sensor demonstrating cross-sensitivity in accordance with one embodiment.

FIG. 9 illustrates a resistance response 900 of the conventional resistance metal oxide H2 sensor 114. But the H2 sensor 114 may not be able differentiate between two gases, namely H2 and C2H2. FIG. 9 illustrates responses 901, 903 of a conventional resistance sensor exposed to different concentrations of H2 and C2H2 gases. The resistance responses 901, 903 are shown alongside a horizontal axis 902 representative of time and a vertical axis 904 representative of magnitudes of the sensor response. For example, the vertical axis 904 may represent response of the conventional resistance metal oxide H2 sensor. The response 901 represents the presence of C2H2, and the response 903 represents the presence of H2. The response 901 includes responses indicating three different concentrations of C2H2, and the response 903 includes responses indicating three different concentrations of H2. Optionally, more than three or less than three different concentrations of one or more of C2H2 or H2 may be graphically indicated. The response 901 includes the response 906 that is representative of a 100 ppm concentration of C2H2, response 908 that is representative of a 300 ppm concentration of C2H2, and response 910 that is representative of a 500 ppm concentration of C2H2. The response 903 includes response 912 that is representative of a 20 ppm concentration of H2, response 914 that is representative of a 40 ppm concentration of H2, and response 916 that is representative of a 60 ppm concentration of H2. As illustrated in FIG. 9, the H2 sensor is unable to differentiate between the response 910 (500 ppm of C2H2) and the response 912 (20 ppm of H2). For example, FIG. 9 illustrates a well-known cross-sensitivity of C2H2 to H2 as pronounced in a strong response to C2H2 while the sensor is designed as a H2 sensor.

Figures 10A, 10B, 10C:
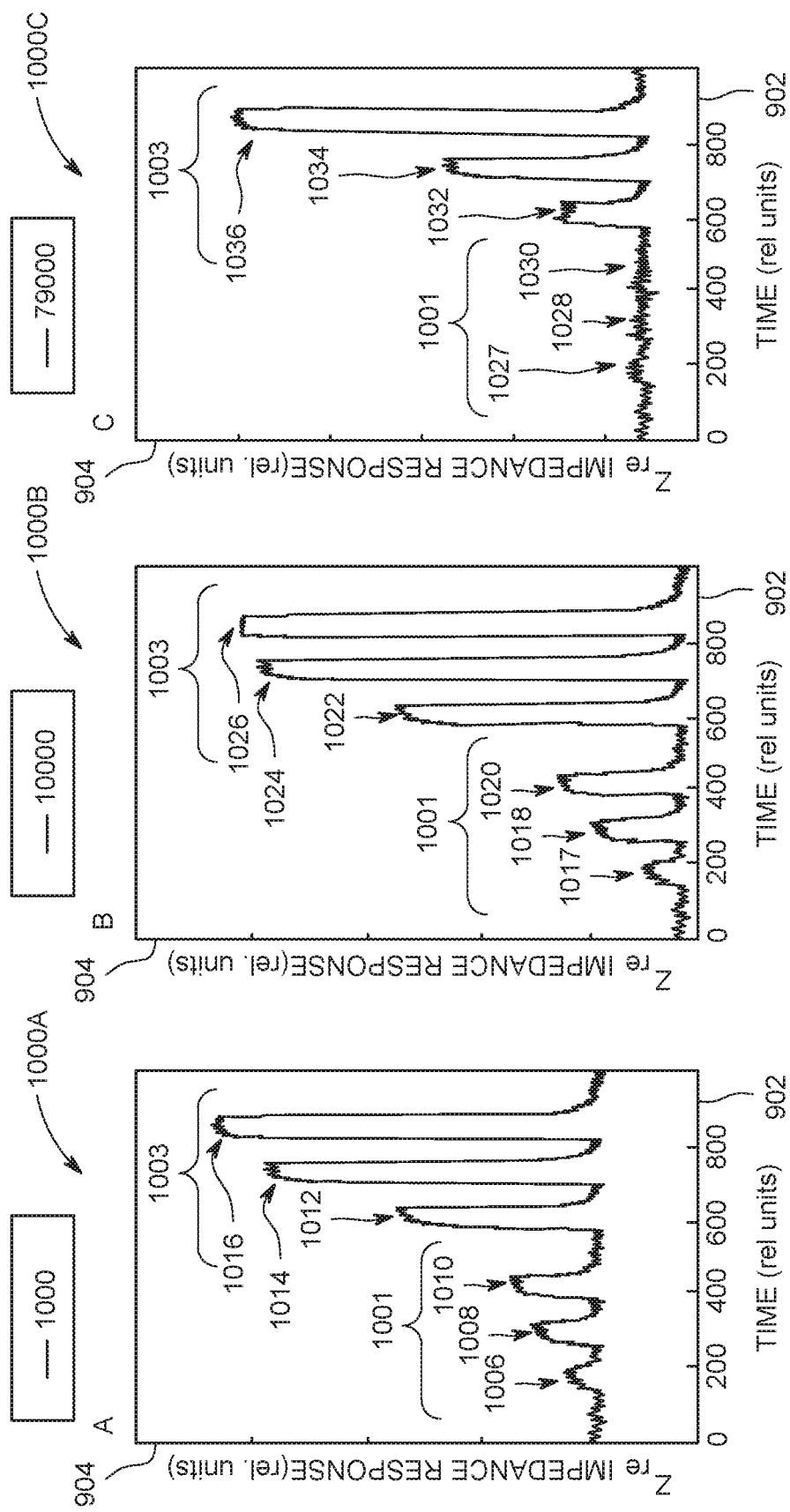
FIG. 10A illustrates a graphical illustration of measured responses corresponding to a real impedance response of a sensor having a first excitation condition in accordance with one embodiment.
FIG. 10B illustrates a graphical illustration of measured responses corresponding to a real impedance response of a sensor having a second excitation condition in accordance with one embodiment.
FIG. 10C illustrates a graphical illustration of measured responses corresponding to a real impedance response of a sensor having a third excitation condition in accordance with one embodiment.

FIGS. 10A, 10B, and 10C illustrate the real part of the impedance responses Zre 1000A, 1000B, 1000C of the H2 sensor 114 at three different frequencies. Optionally, less than three or more than three different frequencies may be used as different excitation conditions. Impedance response 1001 represents the impedance response to the presence of C2H2, and impedance response 1003 represents the impedance response to the presence of H2.

FIG. 10A illustrates the real part of the impedance responses Zre 1001, 1003 with the sensing material 308 subjected to a first excitation and measurement condition. The first excitation and measurement condition includes interrogating the sensing material 308 at frequency 1,000 Hz. The response 1001 includes impedance response 1006 (100 ppm of C2H2), impedance response 1008 (300 ppm of C2H2), and impedance response 1010 (500 ppm of C2H2). The response 1003 includes impedance response 1012 (20 ppm of H2), impedance response 1014 (40 ppm of H2), and impedance response 1016 (60 ppm of H2). Under the first excitation and measurement condition of 1,000 Hz of FIG. 10A, the H2 sensor demonstrates an improved selectivity to H2 compared to C2H2. For example, the impedance response 1010 (500 ppm of C2H2) is graphically distinguishable from the response 1012 (20 ppm of H2).

FIG. 10B illustrates the real part of the impedance responses Zre 1001, 1003 with the sensing material 308 subjected to a second excitation and measurement condition. The second excitation and measurement condition includes interrogating the sensing material 308 at frequency 10,000 Hz. The response 1001 includes impedance response 1017 (100 ppm of C2H2), impedance response 1018 (300 ppm of C2H2), and impedance response 1020 (500 ppm of C2H2). The response 1003 includes impedance response 1022 (20 ppm of H2), impedance response 1024 (40 ppm of H2), and impedance response 1026 (60 ppm of H2). Under the second excitation and measurement condition of 10,000 Hz of FIG. 10B, the H2 sensor demonstrates an improved selectivity to H2 compared to C2H2. For example, the response 1020 (500 ppm of C2H2) is even more graphically distinguishable from the response 1022 (20 ppm of H2) compared to the impedance responses to the excitation condition of FIG. 10A.

FIG. 10C illustrates the real part of the impedance responses Zre 1001, 1003 with the sensing material 308 subjected to a third excitation and measurement condition. The third excitation and measurement condition includes interrogating the sensing material 308 at frequency 79,000 Hz. The response 1001 includes impedance response 1027 (100 ppm of C2H2), impedance response 1028 (300 ppm of C2H2), and impedance response 1030 (500 ppm of C2H2). The response 1003 includes impedance response 1032 (20 ppm of H2), response 1034 (40 ppm of H2), and response 1036 (60 ppm of H2). Under the third excitation and measurement condition of 79,000 Hz of FIG. 10C, the H2 sensor demonstrates an even more improved selectivity to H2 compared to C2H2. For example, the response 1030 (500 ppm of C2H2) is even more graphically distinguishable from the response 1032 (20 ppm of H2) compared to the impedance responses to the excitation conditions of FIGS. 10A and 10B.

Under the first, second and third excitation and measurement condition of FIGS. 10A, 10B, and 10C, the H2 sensor demonstrates a significantly enhanced selectivity to H2 as compare to the C2H2 response.

Figures 11A, 11B, 11C:
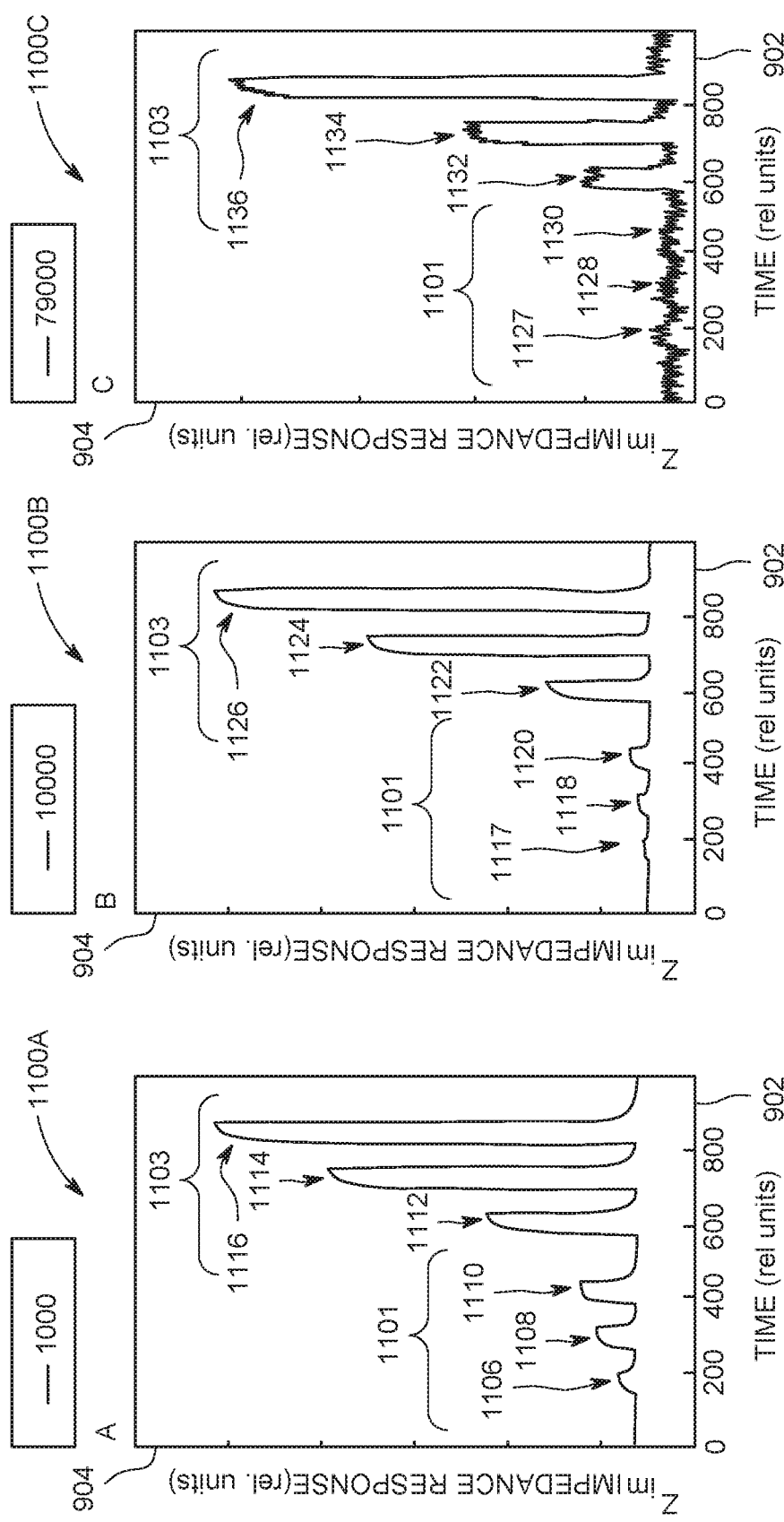
FIG. 11A illustrates a graphical illustration of measured responses corresponding to an imaginary impedance response of a sensor having a first excitation condition in accordance with one embodiment.
FIG. 11B illustrates a graphical illustration of measured responses corresponding to an imaginary impedance response of a sensor having a second excitation condition in accordance with one embodiment.
FIG. 11C illustrates a graphical illustration of measured responses corresponding to an imaginary impedance response of a sensor having a third excitation condition in accordance with one embodiment.

Similarly, FIGS. 11A, 11B, and 11C illustrate the imaginary part of the impedance responses Zim 1100A, 1100B, 1100C of the $H_2$ sensor 114 at three different frequencies. Optionally, less than three or more than three different frequencies may be used as different excitation conditions. Impedance response 1101 (corresponding to the response 1001) represents the impedance response to the presence of C2H2, and impedance response 1103 (corresponding to the response 1003) represents the impedance response to the presence of H2.

FIG. 11A illustrates the imaginary part of the impedance responses Zim 1101, 1103 with the sensing material 308 subjected to the first excitation and measurement condition. The first excitation and measurement condition includes interrogating the sensing material 308 at frequency 1,000 Hz. The response 1101 includes impedance response 1106 (100 ppm of C2H2), impedance response 1108 (300 ppm of C2H2), and impedance response 1110 (500 ppm of C2H2). The response 1103 includes impedance response 1112 (20 ppm of H2), impedance response 1114 (40 ppm of H2), and impedance response 1116 (60 ppm of H2). Under the first excitation and measurement condition of 1,000 Hz of FIG. 11A, the H2 sensor demonstrates an improved selectivity to H2 compared to C2H2. For example, the impedance response 1110 (500 ppm of C2H2) is graphically distinguishable from the response 1112 (20 ppm of H2).

FIG. 11B illustrates the imaginary part of the impedance responses Zim 1101, 1103 with the sensing material 308 subjected to the second excitation and measurement condition. The second excitation and measurement condition includes interrogating the sensing material 308 at frequency 10,000 Hz. The response 1101 includes impedance response 1116 (100 ppm of C2H2), impedance response 1118 (300 ppm of C2H2), and impedance response 1120 (500 ppm of C2H2). The response 1103 includes impedance response 1122 (20 ppm of H2), impedance response 1124 (40 ppm of H2), and impedance response 1126 (60 ppm of H2). Under the second excitation and measurement condition of 10,000 Hz of FIG. 11B, the H2 sensor demonstrates an improved selectivity to H2 compared to C2H2. For example, the response 1120 (500 ppm of C2H2) is even more graphically distinguishable from the response 1122 (20 ppm of H2) compared to the impedance responses to the excitation condition of FIG. 11A.

FIG. 11C illustrates the imaginary part of the impedance responses Zim 1101, 1103 with the sensing material 308 subjected to the third excitation and measurement condition. The third excitation and measurement condition includes interrogating the sensing material 308 at frequency 79,000 Hz. The response 1101 includes impedance response 1126 (100 ppm of C2H2), impedance response 1128 (300 ppm of C2H2), and impedance response 1130 (500 ppm of C2H2). The response 1103 includes impedance response 1132 (20 ppm of H2), response 1134 (40 ppm of H2), and response 1136 (60 ppm of H2). Under the third excitation and measurement condition of 79,000 Hz of FIG. 11C, the H2 sensor demonstrates an even more improved selectivity to H2 compared to C2H2. For example, the response 1130 (500 ppm of C2H2) is even more graphically distinguishable from the response 1132 (20 ppm of H2) compared to the impedance responses to the excitation conditions of FIGS. 11A and 11B.

Under the first, second and third excitation and measurement condition of FIGS. 11A, 11B, and 11C, the H2 sensor demonstrates a significantly enhanced selectivity to H2 as compared to the C2H2 response. Additionally, the impedance imaginary response 1103 to H2 demonstrates a linear response with high sensitivity to H2 at the small concentrations of H2.

Figure 12:
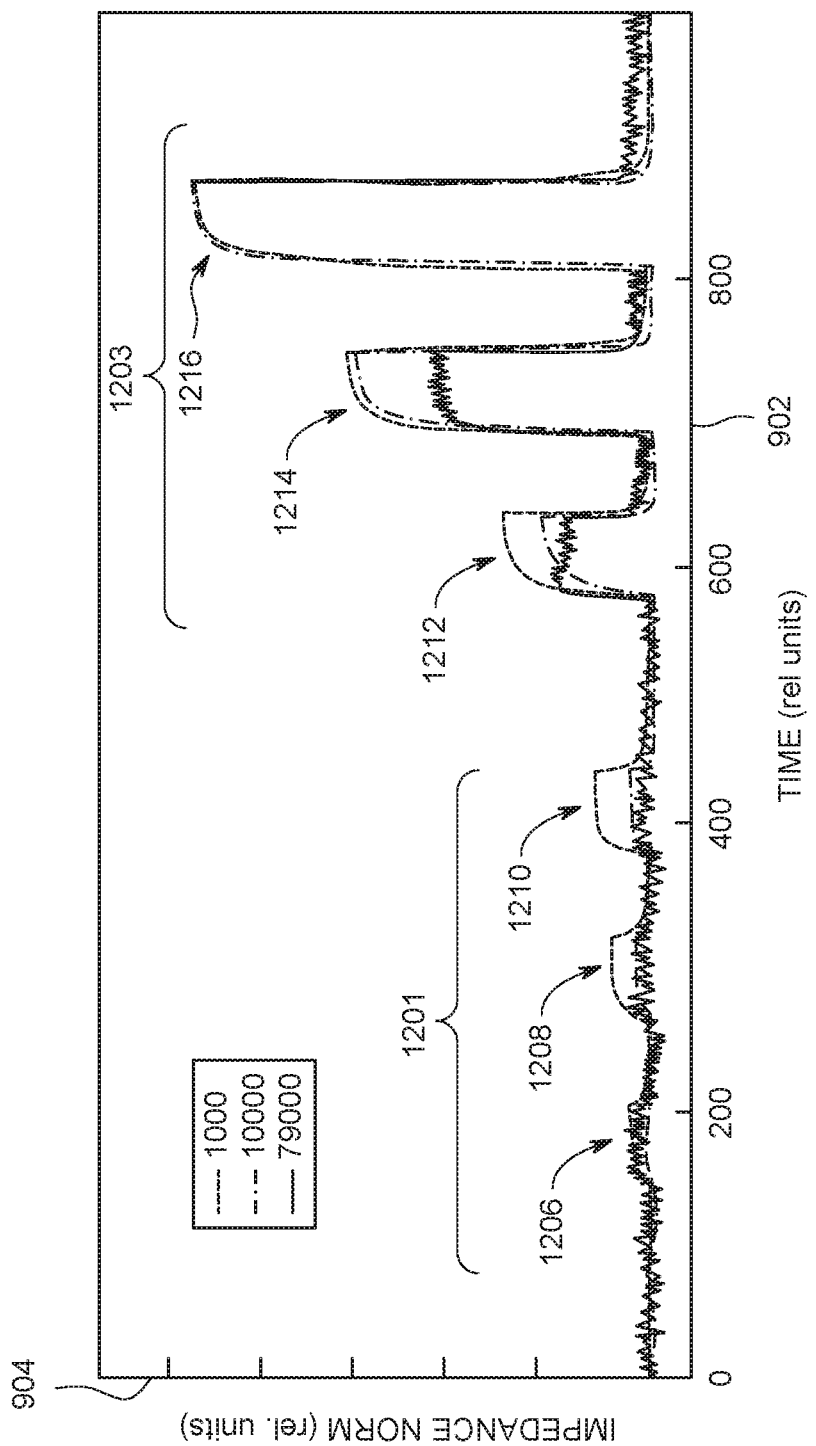
FIG. 12 illustrates a graphical illustration of measured responses corresponding to normalized imaginary impedance responses of a sensor in accordance with one embodiment.

FIG. 12 illustrates normalized imaginary part impedance responses Zim 1201, 1203 (corresponding to the responses 1100A, 1100B, 1100C of FIGS. 11A, 11B, and 11C) illustrating the first, second, and third excitation and measurement condition (1,000 Hz, 10,000 Hz, and 79,000 Hz) normalized to the intensity of the H2 sensor response to 60 ppm of H2 (e.g., responses 1116, 1126, 1136 of FIGS. 11A-C). The response 1201 includes impedance response 1206 that is representative of the 100 ppm concentration of C2H2, impedance response 1208 that is representative of the 300 ppm concentration of C2H2, and impedance response 1210 that is representative of the 500 ppm concentration of C2H2. The response 1103 includes impedance response 1212 that is representative of the 20 ppm concentration of H2, impedance response 1214 that is representative of the 40 ppm concentration of H2, and impedance response 1216 that is representative of the 60 ppm concentration of H2. The imaginary part of the impedance responses Zim demonstrates that with the increasing frequency excitation and measurement condition, the rejection of the C2H2 interference improves. For example, the impedance response 1210 (500 ppm C2H2) is graphically discernable from the impedance response 1212 (20 ppm of H2).

Returning to FIG. 9, and reviewing with respect to FIG. 12, FIG. 12 illustrates that the imaginary part impedance response Zim 1210 (500 ppm of C2H2) is discernable from the imaginary part impedance response 1212 (20 ppm H2). For example, the impedance responses of the H2 sensor illustrate that the H2 sensor, under varying excitation conditions, can discriminate the presence of C2H2 from the presence of H2 of the sample. Alternatively, the resistance responses 901, 903 of FIG. 9 illustrate that the resistor response 910 (500 ppm of C2H2) is not graphically discernable from the resistor response 912 (20 ppm of H2). For example, the resistance sensor demonstrates that the response 910 to 500 ppm of C2H2 interference is the same as the response 912 to 20 ppm of H2.

Figure 13:
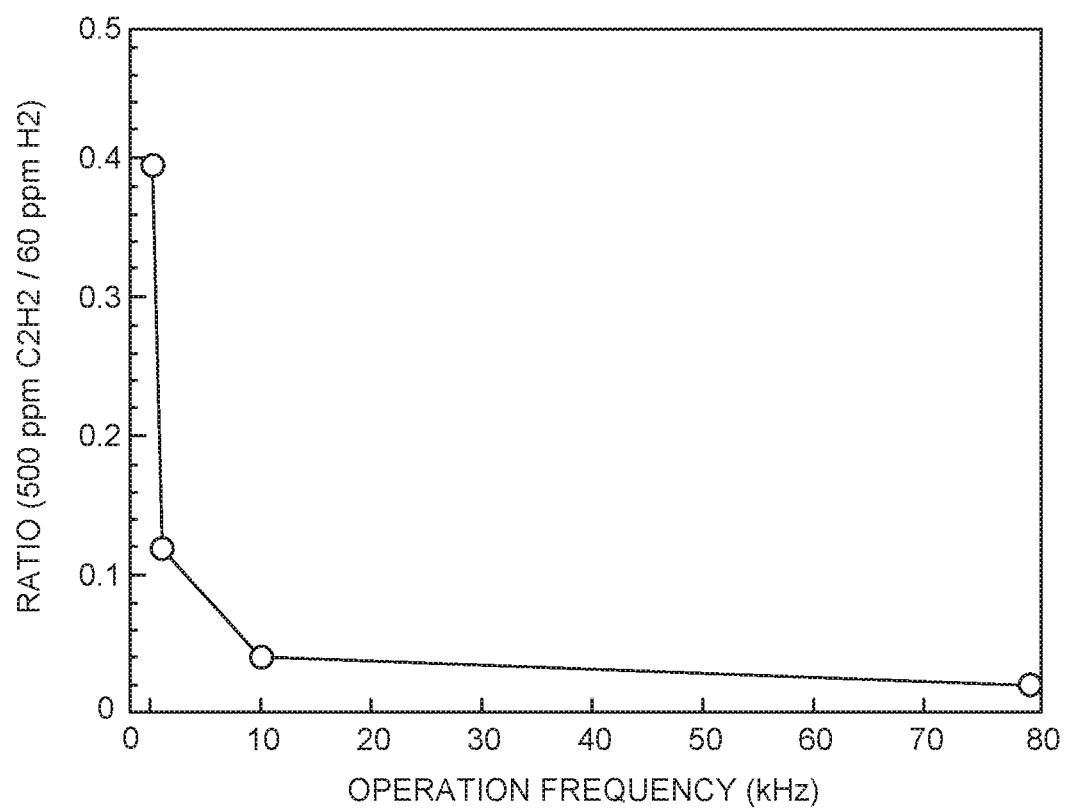
FIG. 13 illustrates a graphical illustration of a ratio of sensor responses in accordance with one embodiment.

FIG. 13 illustrates a graphical illustration of a ratio between the impedance sensor responses to the concentration level of 500 ppm of C2H2 (e.g., impedance responses 1010, 1020, 1030, 1110, 1120, 1130 of FIGS. 10A, B, C and 11A, B, C) and the impedance sensor responses to the concentration level of 60 ppm of H2 (e.g., impedance responses 1016, 1026, 1036, 1116, 1126, 1136 of FIGS. 10A, B, C and 11A, B, C). A horizontal axis 1302 is representative of the operation frequency (e.g., excitation and measurement condition) and a vertical axis 1304 is representative of the ratio between the sensor responses of 500 ppm C2H2 to the sensor responses of 60 ppm of H2 when measurements are performed in a DC mode (e.g., as resistance) and at the excitation and measurement condition 1,000 Hz, 10,000 Hz, and 79,000 Hz. As the operation frequency increases, the ratio between the sensor response to concentrations of 500 ppm of C2H2 and 60 ppm of H2 decreases. As the ratio decreases, the H2 sensor becomes less sensitive to C2H2. For example, as the ratio between the sensor response to concentrations of 500 ppm of C2H2 and 60 ppm of H2 decreases, the interference of C2H2 decreases and the H2 sensor more easily discriminates the C2H2 from the H2. For example, the rejection of C2H2 interference improves.

FIGS. 9-13 illustrate one example of an H2 impedance gas sensor demonstrating an impedance response at varying frequencies in order to improve sensor sensitivity to H2 and reduce the interference of C2H2. For example, sensor sensitivity can include the measured sensor response signals per analyte concentration unit that may also be defined as the ratio of the measured sensor response signals to the measured analyte concentration. Additionally or alternatively, the sensor may be an impedance sensor for one or more different analyte gases. For example, the sensor may improve sensitivity of a second analyte gas of interest of the sensing material while reduce interference of one or more additional analyte gases.

Figure 14:
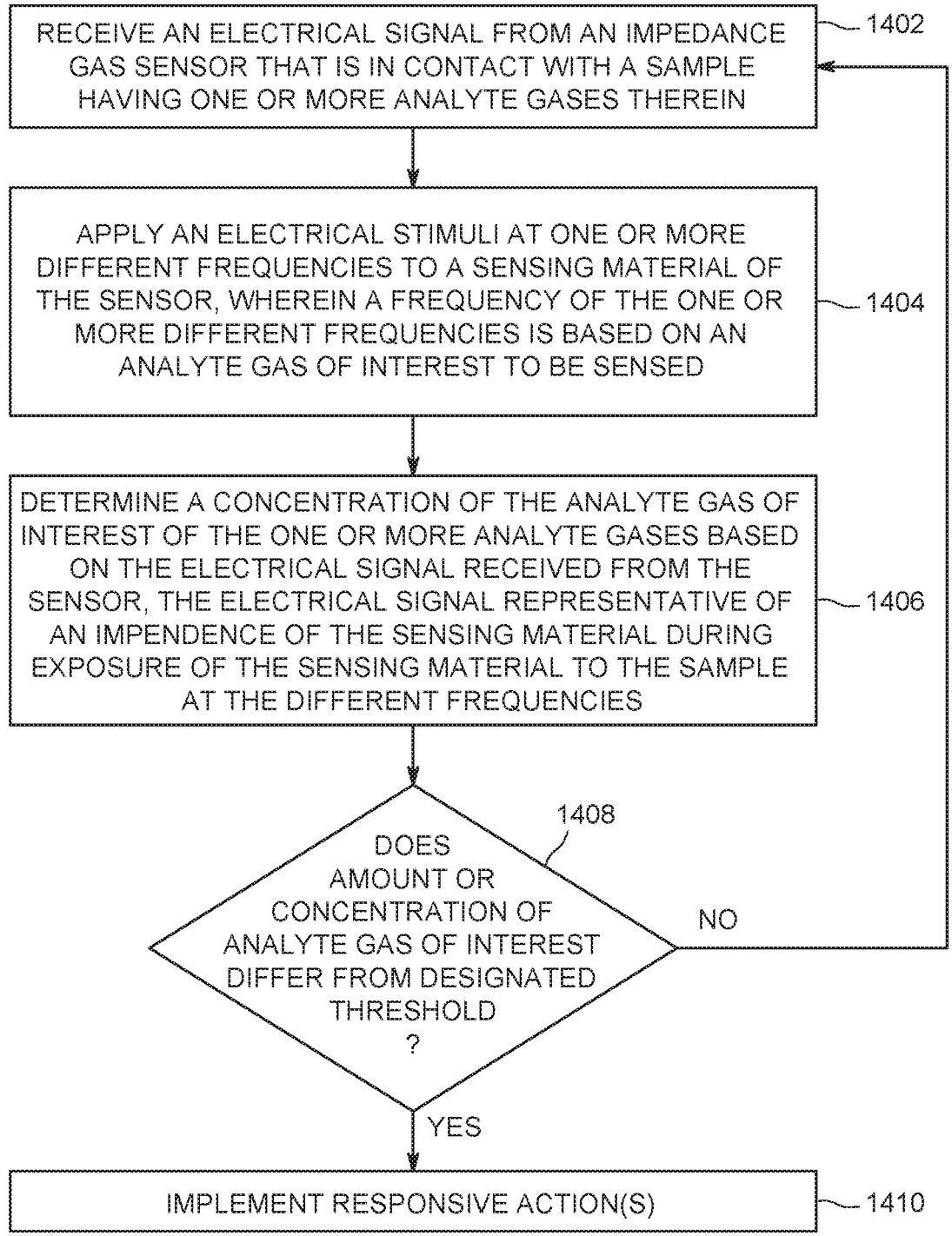
FIG. 14 illustrates a flowchart of one embodiment of a method for sensing one or more analyte gases of interest in accordance with one embodiment.

FIG. 14 illustrates a flowchart of one embodiment of a method 1400 for improved sensing sensitivity. The method 1400 is performed by one or more embodiments of the impedance gas sensing system described herein. At 1402, an electrical signal from an impedance gas sensor is received by one or more processors. The sensor includes electrodes and a sensing region circuit having a sensing material and is in contact with a sample having one or more analyte gases therein. For example, the sample may be transformer oil having dissolved gases in the oil at different concentrations. The dissolved gases may be one or more of CO, CO2, H2, CH4, C2H2, C2H4, or C2H6. At 1404, an electrical stimuli having one or more different frequencies is applied to the sensing material that is in operational contact with the sample. For example, the sensor 114 may be in operational contact with the insulating fluid by immersing the sensor in the insulating fluid, placing the sensor in a headspace of the insulation fluid, or by an alternative method. When the sensor is in operational contact with the oil, dissolved gases in oil interact with the sensor and produce a predictable multivariable sensor response. The operational contact may be achieved by direct immersion of the sensor into oil when the sensing material is wetted by oil or through a gas permeable membrane that may allow dissolved gases in oil to diffuse through the membrane to the sensing material while the oil is not wetting the sensing material or by placing the sensor in the headspace. The operational contact may be also achieved when the sensor is placed in a gas phase sample, wherein the gas phase sample is one or more of extracted from or representative of a dissolved gas content in the insulating fluid. For example, the sensor may be in operational contact with the oil (e.g., the insulating fluid) by immersing the gas sensor in the oil or placing the sensor in a gas phase sample that is extracted from, or representative of, the dissolved gas content in the oil A frequency of the one or more different frequencies is based on a sensing material of the sensor and an analyte gas of interest to be sensed by the sensor. For example, the analyte gas of interest may be H2. The frequency at which the electrodes apply the electrical stimuli is based on the H2 analyte gas of interest. Alternatively, a different frequency may be based on a different analyte gas of interest, for example C2H2.

At 1406, a concentration of the analyte gas of interest is determined based on the electrical signal received from the sensor and on the previously developed and stored transfer function between the multivariable response of the sensor and analyte concentrations. For example, the sensor transfer function can include a relationship between the sensor response signal and the analyte gas concentration used to determine the analyte gas concentration in different applications of the sensor. The electrical signal is representative of an impedance of the sensing material during exposure of the sensing material to the sample at the one or more different frequencies, wherein the impedance of the sensing material indicates a concentration of the analyte gas of interest. For example, the electrical signal may be a first impedance response, wherein the first impedance response may indicate a first concentration of H2 present in the sample.

At 1408, a determination is made as to whether the determined concentration of the analyte gas of interest differs from one or more designated thresholds. For example, the analyte gas of interest may be H2. If the determined concentration of H2 in the sample of transformer oil is less than or greater than a designated threshold concentration or amount of H2, the too low or too high concentration of H2 may indicate previous and/or potential faults with the transformer. As another example, if the determined concentration of methane CH4 exceeds a designated threshold, then the transformer may need to be deactivated or stopped to avoid potential sparking. As another example, if the determined concentrations of one or more of ethylene C2H4, carbon monoxide CO, or carbon dioxide CO2 exceeds a designated threshold, the transformed may need to be deactivated or stopped to avoid severe overheating.

If the determined amount and/or concentration of the analyte gas of interest differs from a designated threshold (e.g., exceeds a larger, upper designated threshold or falls below a smaller, lower designated threshold), then flow of the method 1400 can proceed toward 1410. Otherwise, flow of the method 1400 may return toward 1402 to continue measuring the amount and/or concentration of analyte gases, or may terminate.

At 1410, one or more responsive actions are implemented. For example, if the amount of one or more gases in the oil of a transformer exceeds a designated threshold, then the transformer is automatically deactivated.

Figure 15:
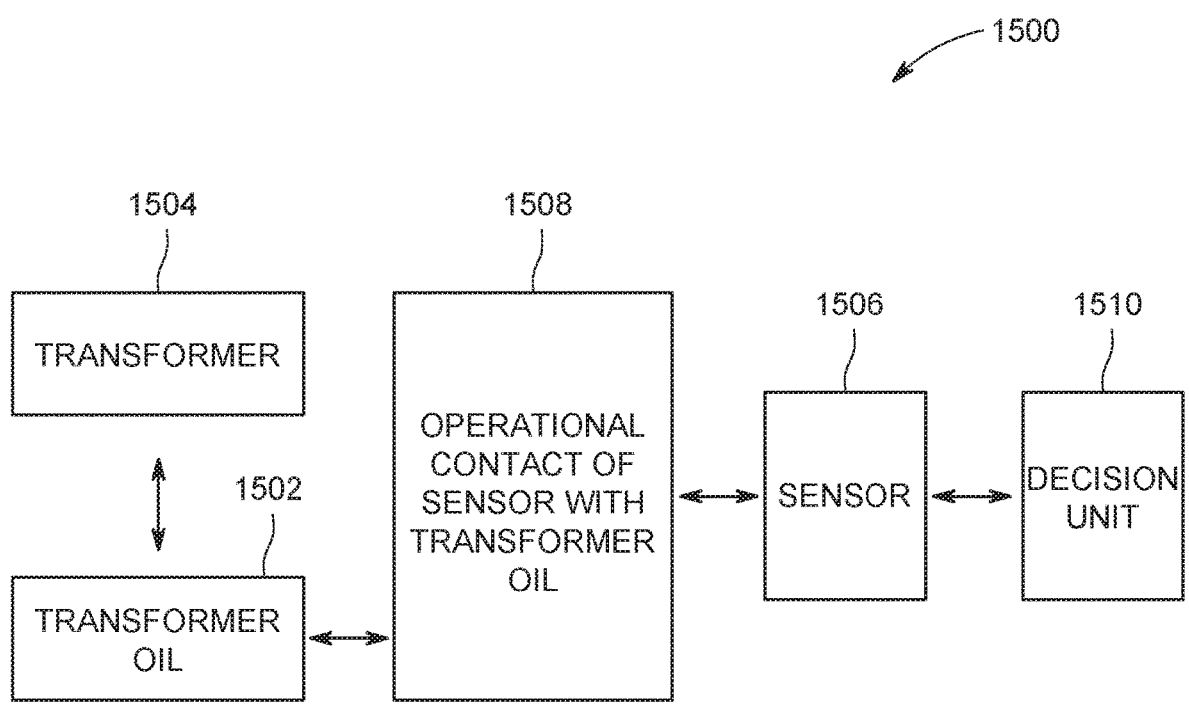
FIG. 15 illustrates a system for measurement of gases dissolved in an insulating fluid in accordance with one embodiment.

FIG. 15 illustrates a system 1500 for measurement of gases dissolved in transformer oil 1502 or any insulating fluid of an electrical transformer 1504 in accordance with one embodiment. Measurements of dissolved gases are performed with at least one multivariable sensor 1506 wherein the sensor 1506 is in operational contact with the oil 1502 or gas that has been released from the insulating fluid, using a method such as membrane interface, headspace method, vacuum extraction, or any alternative method, and exposed to the sensor. For example, the sensor 1506 may be in operational contact with at least one analyte gas from the transformer oil 1502 (e.g., the insulating fluid). A multivariable sensor can refer to a single sensor capable of producing multiple responses, such as response signals, that are not substantially correlated with each other and where these individual response signals from the multivariable sensor are further analyzed using multivariate analysis tools to construct response patterns of sensor exposure to different analytes at different concentrations. The multiple responses from the sensor may differ by sensor operating frequency, sensor operating wavelength, sensor operating temperature, sensor operating voltage, sensor operating power, sensor operating polarization, or the like. A multivariable sensor can be any sensor. A conventional sensor can be converted into a multivariable sensor by measuring more than one response such as response signals, that are not substantially correlated, with each other and where individual response signals from the sensor are further analyzed using multivariate analysis tools.

In one or more embodiments, multivariable and/or multivariate signal transduction is performed on the multiple response signals using multivariate analysis tools to construct a multivariable sensor response. A multivariate analysis can refer to a mathematical procedure that may be used to analyze two or more variables from the sensor response and to provide information at the type of at least one gas from the measured sensor parameters and/or quantitative information about the concentration of at least one gas from the measured sensor parameters. For example, the multivariate analysis tools may include canonical correlation analysis, regression analysis, nonlinear regression analysis, principal components analysis, discriminate function analysis, multidimensional scaling, linear discriminate analysis, logistic regression, neural network analysis, or another tool. The multivariate analysis may be performed online, inline, and/or offline.

In one or more embodiments, dissolved gases in oil 1502 interact with the sensor 1506, or are released from the oil and exposed to the sensor 1506, and produce a predictable multivariable sensor response. The operational contact 1508 may be achieved by direct immersion of the sensor 1506 into oil 1502 when the sensor 1506 is wetted by the oil or through a gas permeable membrane that may allow dissolved gases in oil 1502 to diffuse through the membrane to the sensor 1506 while the oil 1502 is not wetting the sensor 1502. The operational contact 1508 may be also achieved when the sensor 1506 is arranged in an air gap between oil 1502 and the sensor 1506. Such air gap may be formed by using the membrane and a gap between the membrane and the sensor 1506 or by positioning the sensor 1506 above the highest level of oil that is incompletely filling a reservoir. The operational contact may also be achieved through an alternative gas extraction method from the insulating fluid such as headspace or vacuum extraction and extracted gas exposed to the sensor 1506.

The sensor 1506 is a multivariable sensor capable of producing multiple response signals that are not substantially correlated with each other and where these individual response signals from the multivariable sensor 1506 are further analyzed using multivariate analysis tools to construct response patterns of sensor exposure to different analytes dissolved in oil at different concentrations.

Nonlimiting examples of a multivariable sensor used in FIG. 15 include impedance sensors, resonant impedance sensors, non-resonant impedance sensors, electronic sensors, electro-mechanical resonator sensors (e.g., tuning forks, cantilever sensors, acoustic device sensors, or the like), optical sensors, acoustic sensors, photoacoustic sensors, near-infrared sensors, ultraviolet sensors, infrared sensors, visible light sensors, fiber-optic sensors, reflection sensors, or the like.

The multivariable sensor 1506 may produce multiple response signals that may be used by a decision unit 1510 for control purposes. The multiple response signals of the multivariable sensor 1506 may be analyzed by the sensor electronics itself and may produce a composite output based on the multivariate analysis of the multiple response signals. For example, the decision unit 1510 may receive the multiple responses from the sensor 1506 during exposure of the sensor 1506 to the analyte gas from the transformer oil 1502 (e.g., the insulating fluid). The multiple response signals may be representative of a concentration of the analyte gas present in the transformer oil 1502 (e.g., the insulating fluid).

Figure 16:
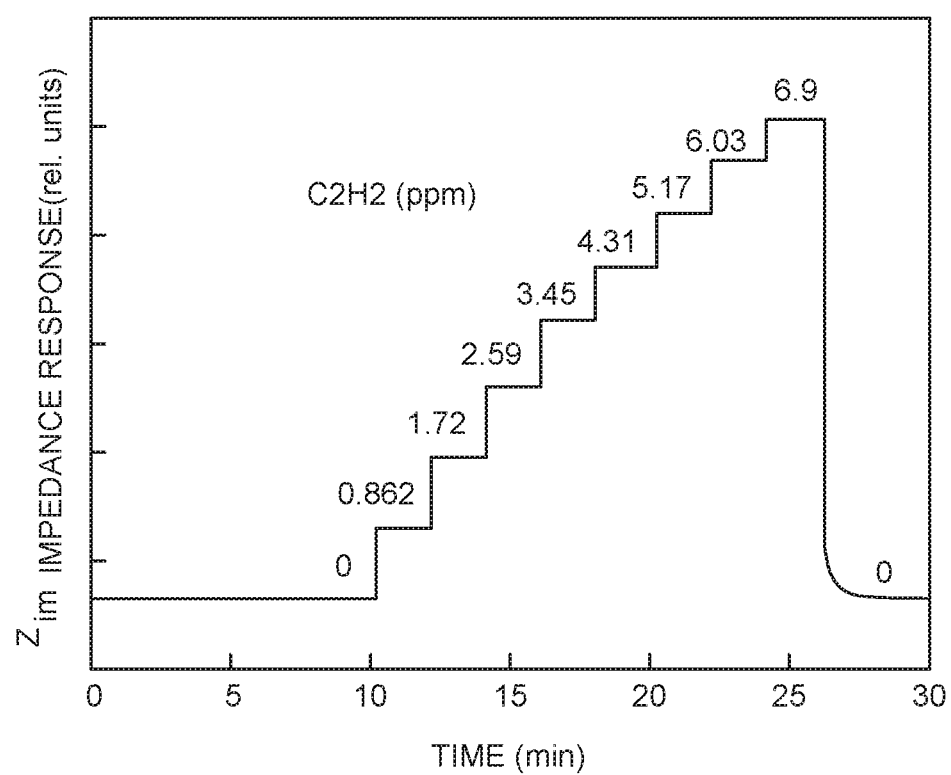
FIG. 16 illustrates a graphical illustration of detection of acetylene at low ppm levels using an impedance sensor accordance with one embodiment.

FIG. 16 illustrates an exemplary detection of low ppm levels of acetylene C2H2 diluted with air using a sensor of this invention. The sensor utilizes a semiconducting metal oxide as a sensing material. The semiconducting metal oxide was tin dioxide SnO2. Concentrations of C2H2 were generated at sub-ppm and low ppm levels such as 0.86, 1.72, 2.59, 3.45, 4.31, 5.17, 6.03, and 6.90 ppm using a computer-controlled gas dilution and mixing system. The sensor was positioned in a low-dead volume gas flow cell. The sensor with a semiconducting metal oxide SnO2 as a sensing material was operated in AC impedance mode. Measurements of the sensor impedance were performed with an impedance analyzer. Results depicted in FIG. 16 illustrate that the sensor operating in impedance mode detected concentrations of C2H2 down to a sub-ppm level of 0.86 ppm.

Figure 17:
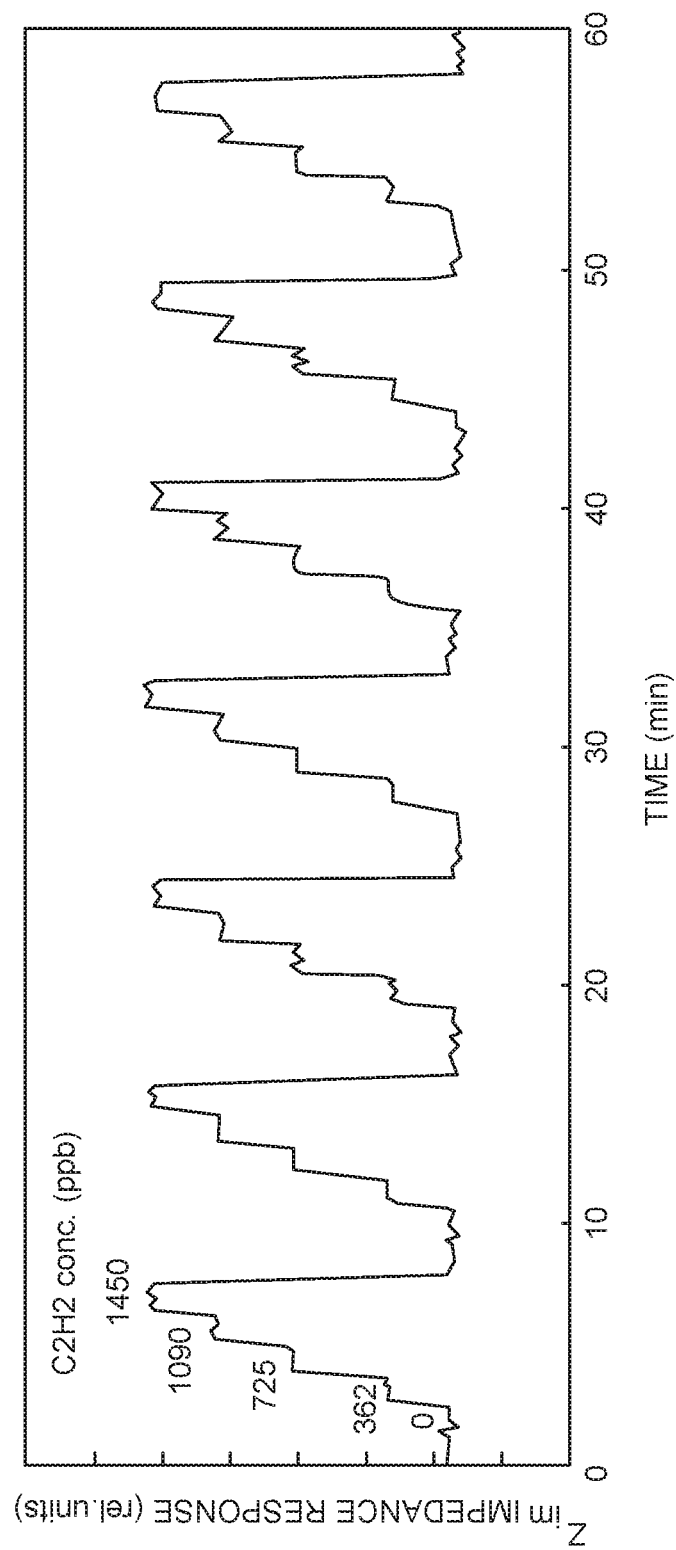
FIG. 17 illustrates a graphical illustration of multiple cycles of detection of acetylene in accordance with one embodiment.

FIG. 17 depicts an example of detection of multiple cycles of acetylene C2H2 at parts per billion (ppb) levels using a sensor of this invention. The sensor utilized a semiconducting metal oxide as a sensing material. The semiconducting metal oxide was tin dioxide SnO2. Multiple cycles of concentrations of C2H2 were generated at ppb levels such as 0, 362, 725, 1090, and 1450 ppb using a computer-controlled gas dilution and mixing system. The sensor was positioned in a low-dead volume gas flow cell. This sensor with a semiconducting metal oxide SnO2 as a sensing material was operated in impedance mode. Measurements of the sensor impedance were performed with an impedance analyzer. Results depicted in FIG. 17 illustrate that the sensor operating in impedance mode detected concentrations of C2H2 down to a 362 ppb level over multiple cycles of operation.

Figure 18A:
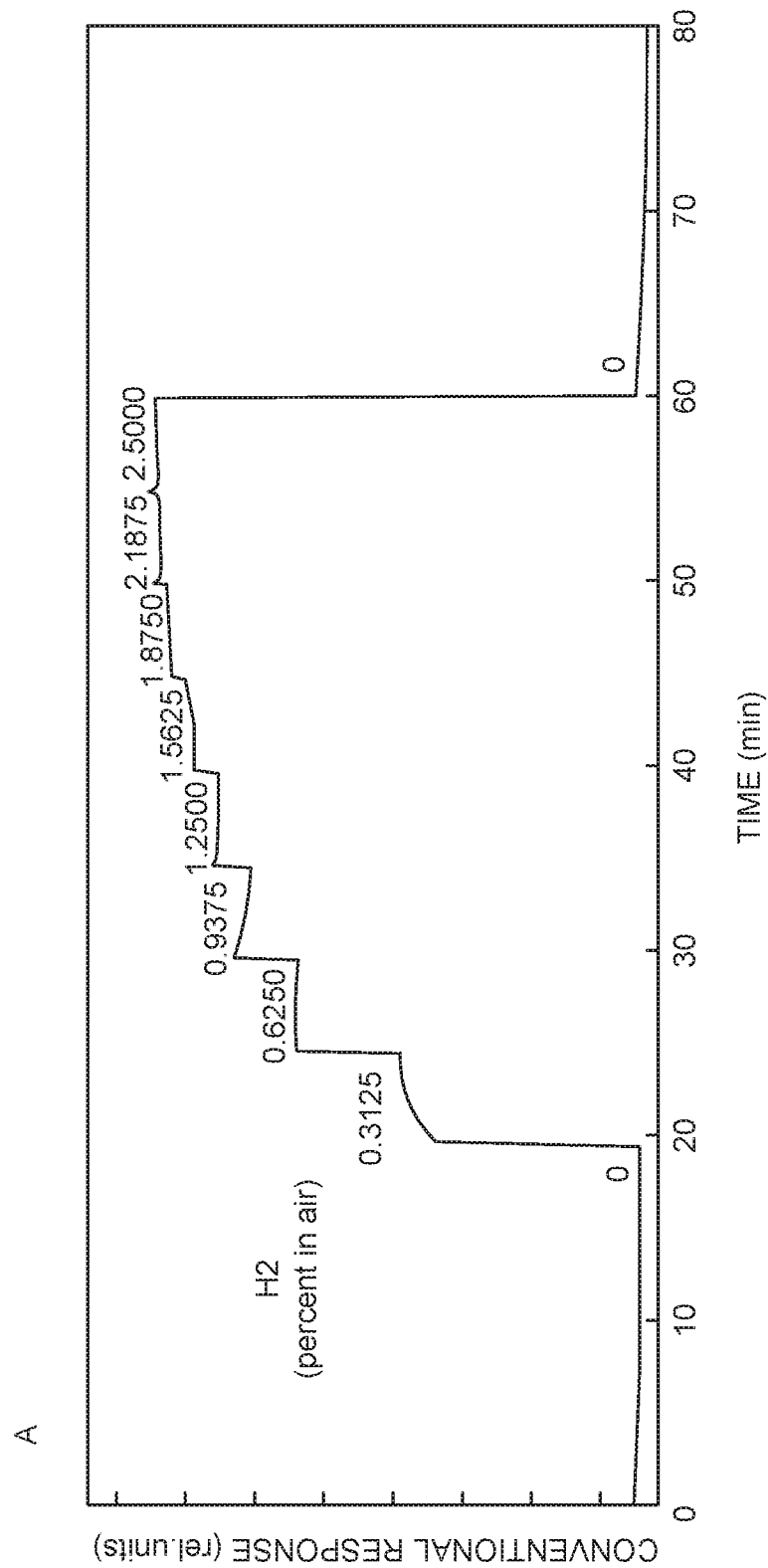
FIG. 18A illustrates a graphical illustration of detection of high concentrations of hydrogen using a sensor operating in resistance mode in accordance with one embodiment.
Figure 18B:
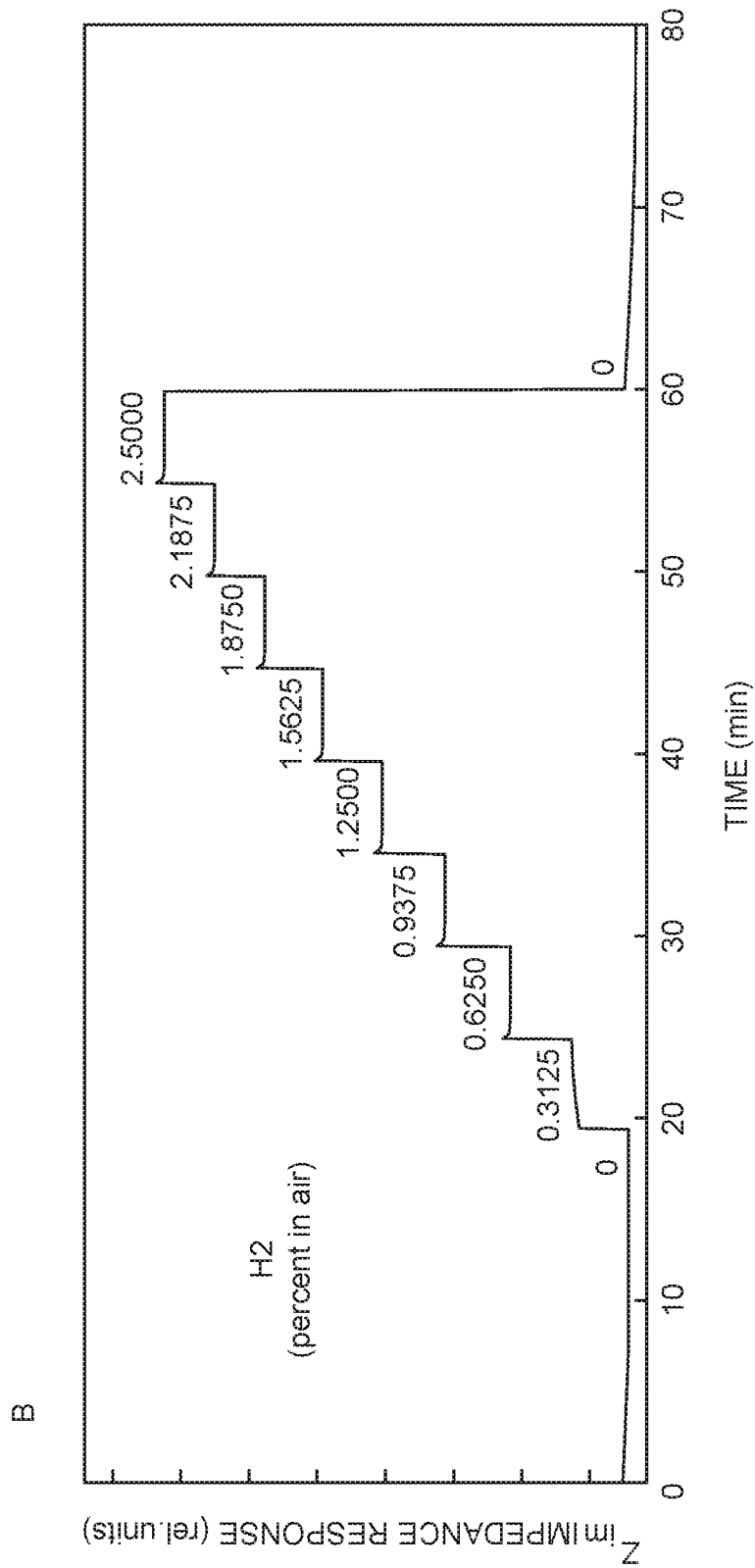
FIG. 18B illustrates a graphical illustration of detection of high concentrations of hydrogen using a sensor operating in impedance mode in accordance with one embodiment.

FIGS. 18A and 18B depict exemplary time responses of a sensor with a semiconducting metal oxide as a sensing material for detection of different concentrations of hydrogen H2 diluted with air. FIG. 18A illustrates the sensor operating in DC resistance mode, and FIG. 18B illustrates the sensor operating in AC impedance mode. The semiconducting metal oxide was tin dioxide SnO2. Concentrations of H2 were generated at percent levels such as 0, 0.3125, 0.6250, 0.9375, 1.2500, 1.5625, 1.8750, 2.1875, and 2.5000 percent by volume in air using a computer-controlled gas dilution and mixing system. The sensor was arranged in a low-dead volume gas flow cell. Results depicted in FIG. 18A illustrate that the sensor operating in resistance mode (with resistance readout) exhibited a rapid saturation of the response magnitude as a function of H2 concentration. This limitation led to relatively poor sensitivity of the sensor when operating in resistance mode for detection of relatively high concentrations of H2. In contrast to the sensor operating in resistance mode (e.g., FIG. 18A), operation of the same sensor in impedance mode as depicted in FIG. 18B provided an improved sensitivity of the sensor for detection of relatively high concentrations of H2.

Figure 19:
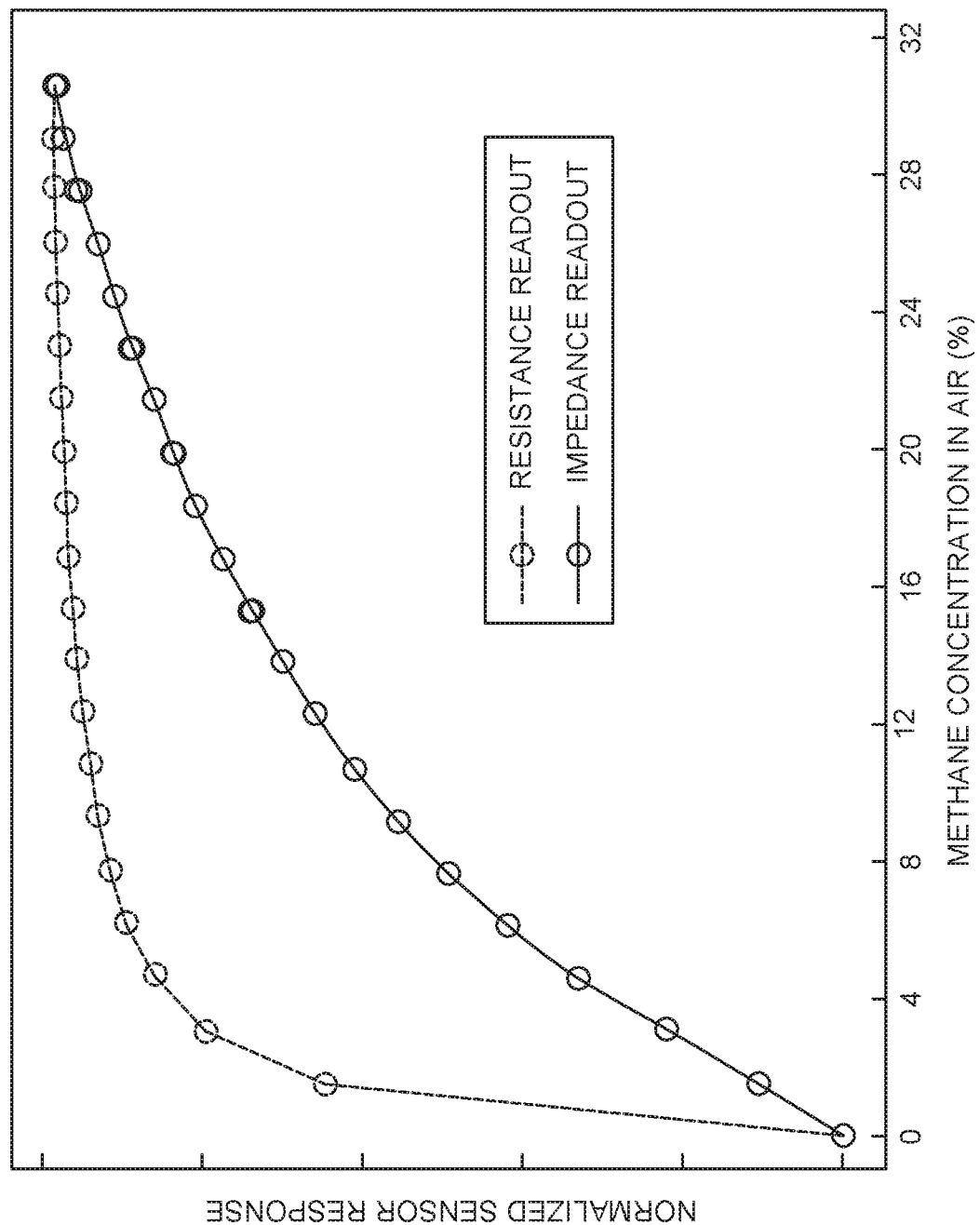
FIG. 19 illustrates a graphical illustration of detection of high concentrations of methane in accordance with one embodiment.

FIG. 19 depicts exemplary calibration curves for detection of methane CH4 diluted with air using a sensor with a semiconducting metal oxide as a sensing material and when operated in DC resistance mode and in AC impedance mode. The semiconducting metal oxide was tin dioxide SnO2. Concentrations of CH4 were generated at percent levels such as 0, 1.54, 3.08, 4.62, 6.15, 7.69, 9.23, 10.8, 12.3, 13.8, 15.4, 16.9, 18.5, 20.0, 21.5, 23.1, 24.6, 26.2, 27.7, 29.2, and 30.8 percent by volume in air using a computer-controlled gas dilution and mixing system. The sensor was arranged in a low-dead volume gas flow cell. Results depicted in FIG. 19 illustrate that the sensor operating in resistance mode exhibited a rapid saturation of the response magnitude as a function of methane CH4 concentration. This limitation led to relatively poor sensitivity of the sensor when operated in resistance mode for detection of relatively high concentrations of methane CH4. In contract to the sensor operating in resistance mode, operation of the same sensor in impedance mode provided an improved sensitivity of the sensor for detection of relatively high concentrations of CH4.

Figure 20A:
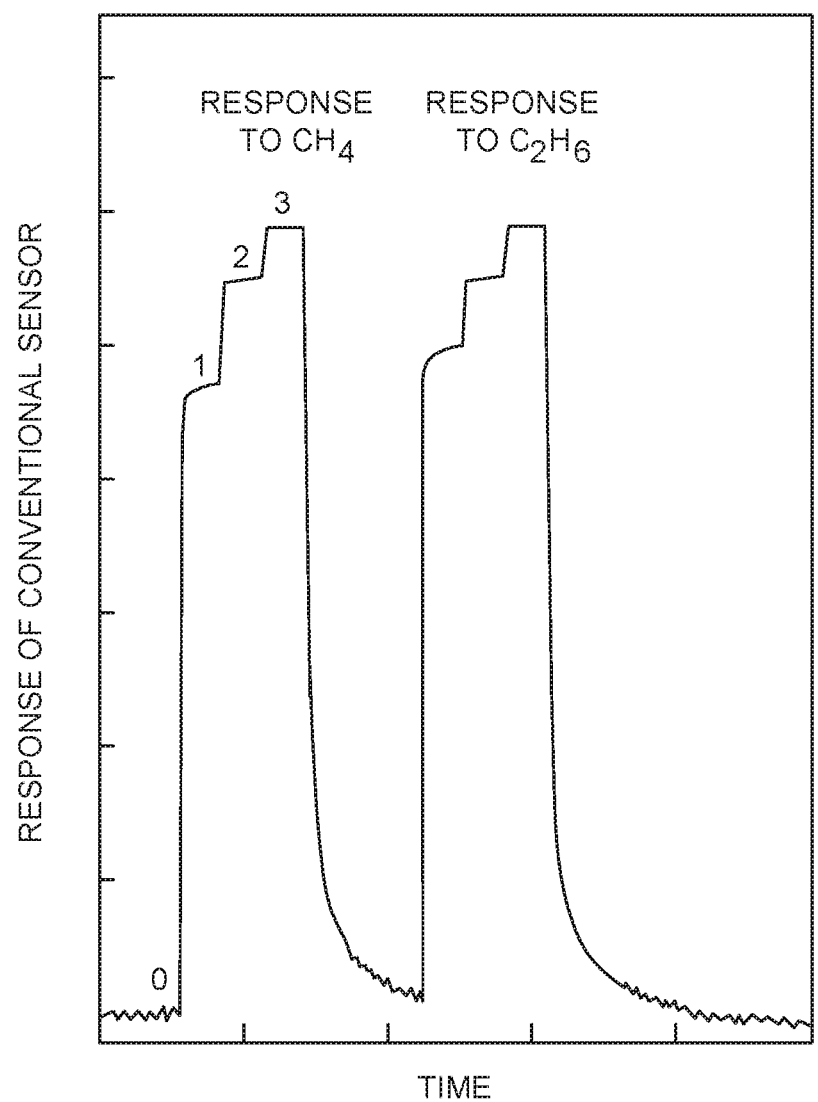
FIG. 20A illustrates a graphical illustration of detection of methane and ethane using a sensor operating in resistance mode in accordance with one embodiment.
Figure 20B:
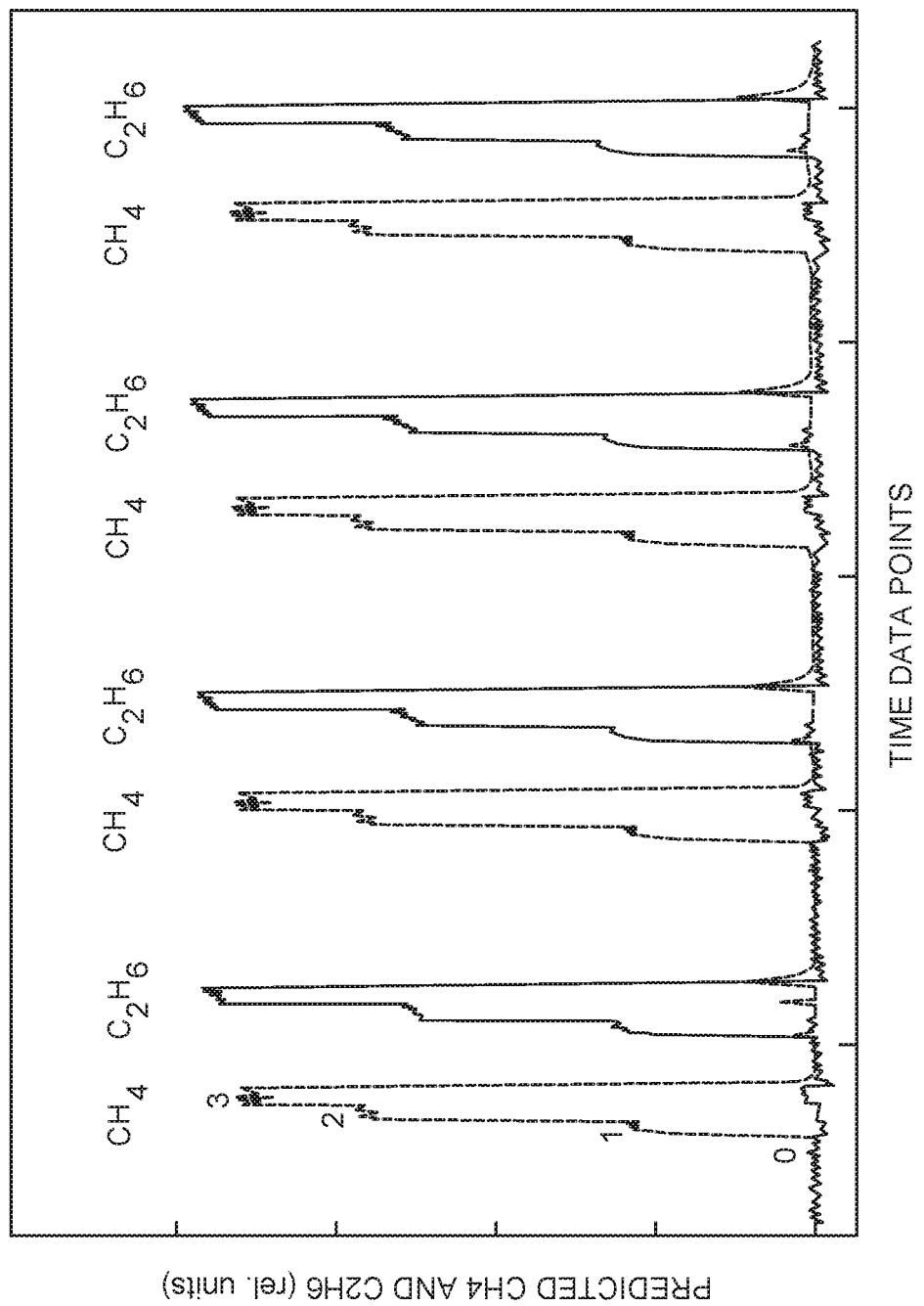
FIG. 20B illustrates a graphical illustration of detection of methane and ethane using developed transfer functions over multiple cycles of periodic exposures of a sensor to methane and ethane with the sensor operating in impedance mode in accordance with one embodiment.

FIGS. 20A and 20B depict an exemplary detection of methane CH4 and ethane C2H6 diluted with air using a sensor with a semiconducting metal oxide as a sensing material. The semiconducting metal oxide was tin dioxide SnO2. The sensor was arranged in a low-dead volume gas flow cell. The sensor with the semiconducting metal oxide SnO2 as the sensing material was operated in DC resistance mode and in AC impedance mode. In the performed experiments, different methane and ethane concentrations were generated using a computer-controlled gas dilution and mixing system. As a non-limiting example, concentrations of methane and ethane were 0, 56, 112, and 169 ppm labeled as 0, 1, 2, and 3 on FIGS. 20A and 20B. Optionally, other concentrations of methane and ethane can also be detected. As expected, when the sensor operated in resistance mode, as illustrated in FIG. 20A, the sensor did not discriminate between methane and ethane.

When the sensor with a semiconducting metal oxide SnO2 as a sensing material was operated in impedance mode, independent quantitation of methane and ethane was achieved. Separate independent quantitation of methane and ethane was performed using a DFSS Process Tool of GE's Six Sigma Toolbox. For this quantitation, responses of a single sensor at several frequencies were entered into the DFSS Process Tool along with the known concentrations of methane and ethane. The DFSS Process Tool computed transfer functions that selectively predicted concentrations of methane and ethane.

The developed transfer function for selective quantitation of methane and the developed transfer function for selective quantitation of ethane were applied for multiple cycles of exposures of the sensor to methane and ethane. FIG. 20B depicts independent quantitation of only methane and only ethane using these transfer functions over multiple cycles. The predicted sensor output for methane was not affected by strong raw sensor responses to ethane and showed only predicted concentrations of methane. The predicted sensor output for ethane was not affected by the raw sensor response to methane and showed only predicted concentrations of ethane.

FIGS. 21A, 21B, 22A, 22B, 23A, and 23B illustrate three embodiments having distinct shapes of sensor impedance responses of the subject matter described herein. As one example, the sensor is a tin dioxide SnO2 metal oxide sensor responding to step changes in hydrogen H2 concentrations ranging from 0 to 1000 ppm in steps of 100 ppm with exposures to clean air in between exposures to H2.

Figure 21A:
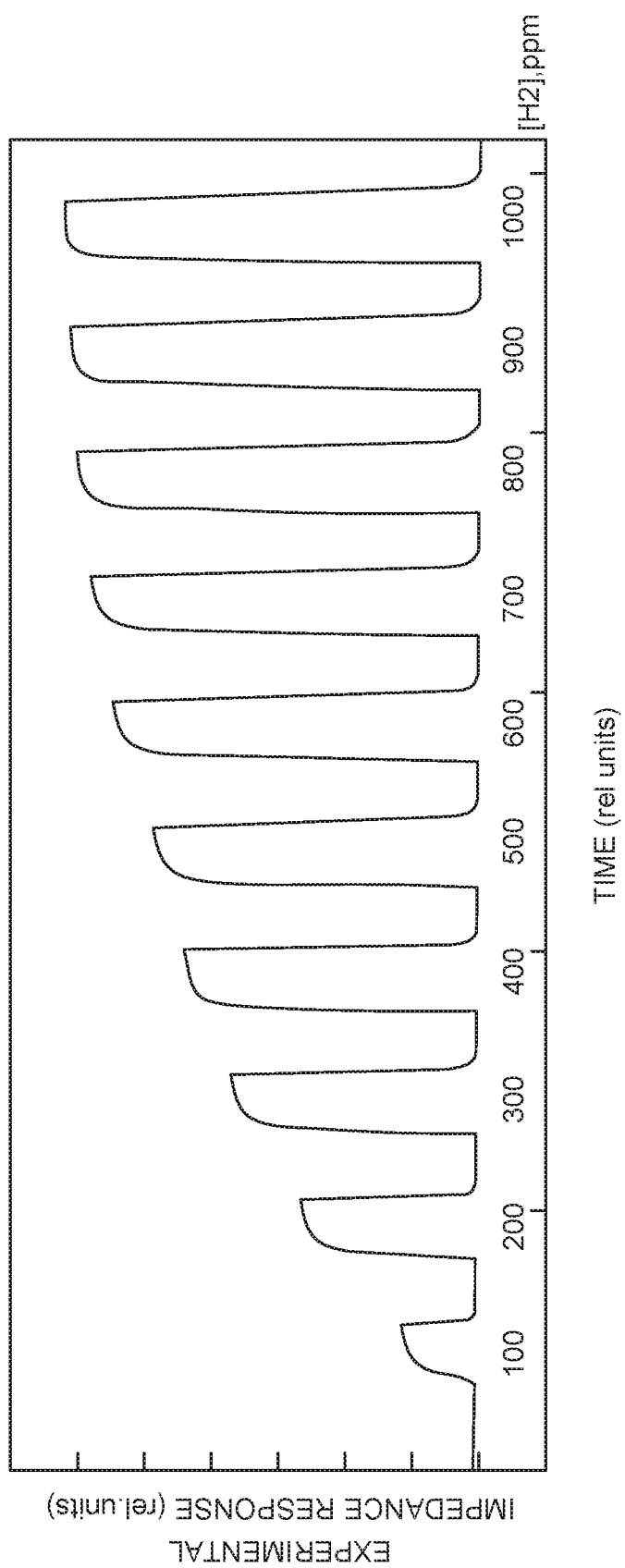
FIG. 21A illustrates a graphical illustration of a measured impedance response of a sensor to different concentrations of hydrogen gas at a first operation frequency of the sensor in accordance with one embodiment.

FIG. 21A illustrates the experimentally measured impedance response of the sensor to different H2 gas concentrations obtained at a first operation frequency of the sensor. For example, the first operation frequency is about 20 kHz. The shape of the impedance response of the sensor is similar to a resistance response of a semiconducting metal oxide upon exposure of the sensor to increasing concentrations of H2 gas in air. The shape of the resistance response to H2 gas may be predictable by a commonly used relation between resistance of a metal oxide sensor and H2 concentrations. A calculated resistance of the impedance response of a metal oxide sensor, such as with a tin dioxide SnO2 or other semiconducting metal oxide to increasing H2 concentrations in air can be described with a power law represented by Eq. (2):

$$R=R_o(1+K_{H2}[H_2]^2)^{-\beta} \qquad \text{Eq. (2)}$$

where Ro may be the sensor resistance to clean air, $K_{H2}$ may be the resistance or impedance sensitivity of the sensor to H2 gas, [H2] may be the concentration of H2 gas presented to the sensor, and β may be the power law coefficient of the sensor response.

Figure 21B:
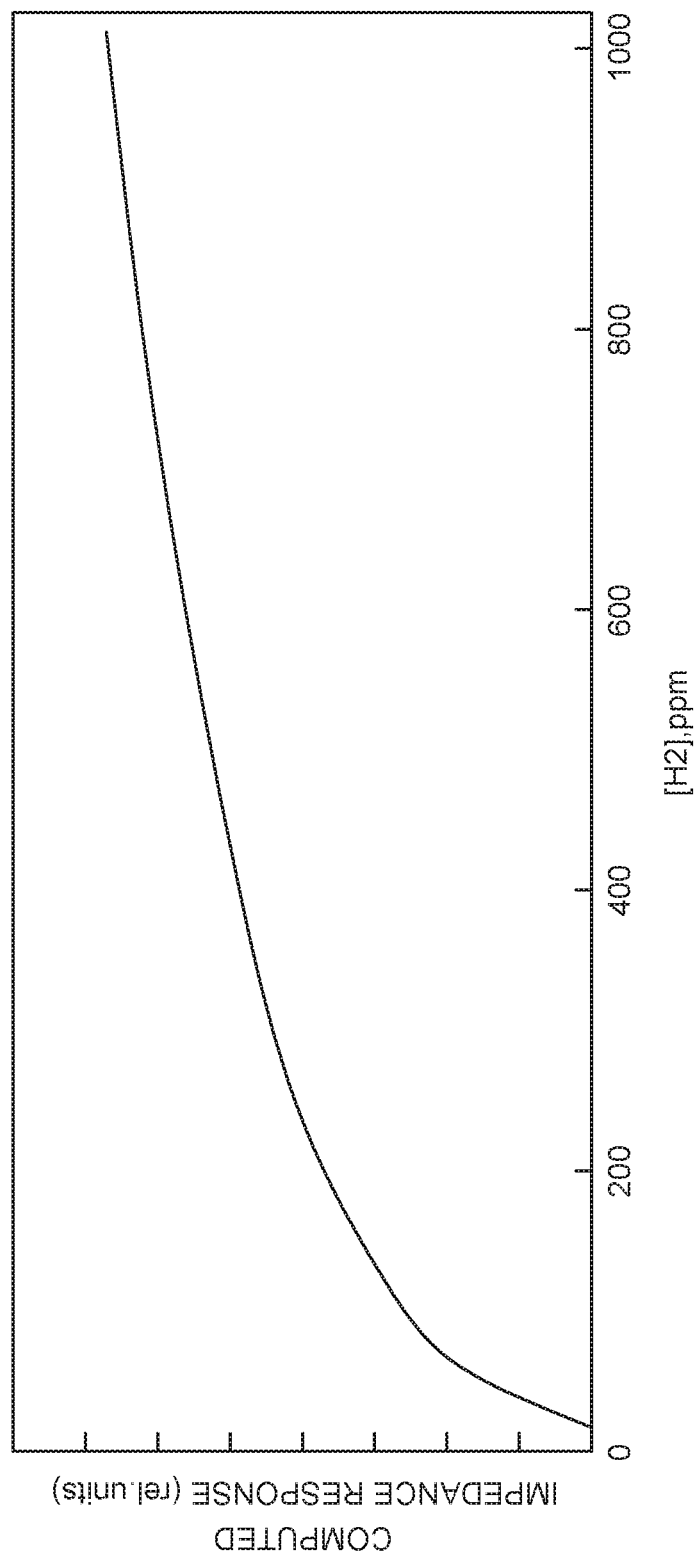
FIG. 21B illustrates a graphical illustration of a calculated impedance response of the sensor of FIG. 21A in accordance with one embodiment.

FIG. 21B illustrates the calculated resistance of the impedance response of the sensor of FIG. 21A. The response illustrated in FIG. 21B is similar to the response of the resistance sensor illustrated in FIG. 5. Comparing the shapes of the responses in FIGS. 21A and 21B demonstrates the resemblance to the response illustrated in FIG. 5, confirming the validity of Eq. (2) above.

The impedance response of the sensor of the subject matter described herein at other frequencies has shapes that are different than the shape of the conventional response of a resistance sensor (e.g., the resistance response of FIG. 5) which is the shape of a known loss of sensor sensitivity at increasing concentrations of H2 gas. FIGS. 22A, 22B, 23A, and 23B illustrates the different shapes of the impedance responses at other frequencies.

Figure 22A:
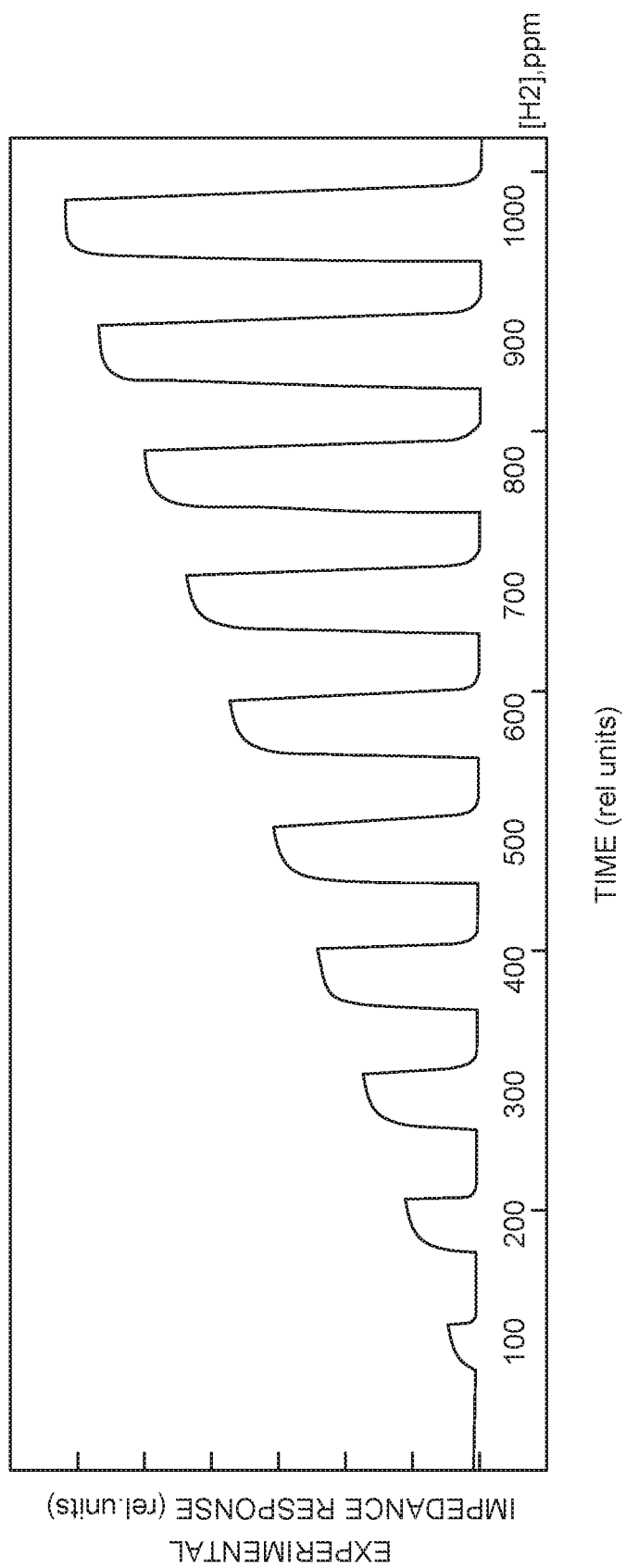
FIG. 22A illustrates a graphical illustration of a measured impedance response of a sensor to different concentrations of hydrogen gas at a second operation frequency of the sensor in accordance with one embodiment.

FIG. 22A illustrates the measured impedance response of the sensor to different H2 gas concentrations obtained at a second operation frequency of the sensor. For example, the second operation frequency may be about 45 kHz. The shape of the impedance response of the sensor is approximately an S-shape and is visually different from the resistance response of the same semiconducting metal oxide upon exposure to increasing concentrations of H2 gas in air illustrated in FIG. 5. Additionally, the S-shape of the impedance response can be alternatively described by the power law equation Eq. (2). For example, a calculated resistance of the impedance response of the metal oxide sensor to increasing H2 concentrations in air of FIG. 22A can also be described with the power law represented by Eq. (2) but with a different coefficient $K_{H2}$ representing the resistance sensitivity of the sensor to H2 gas. For example, the value of the coefficient $K_{H2}$ of the power law calculation in FIG. 22A may be less than the value of the coefficient $K_{H2}$ of the power law calculation of the impedance response of FIG. 21A.

FIG. 22B illustrates the calculated resistance of the impedance response of the sensor of FIG. 22A. A visually comparison of the shapes of the responses illustrated in FIG. 22A and FIG. 22B demonstrates a resemblance to the S-shape of the measured impedance response of the sensor. For example, the different coefficient $K_{H2}$ effects the shape of the sensor impedance response.

Figure 23A:
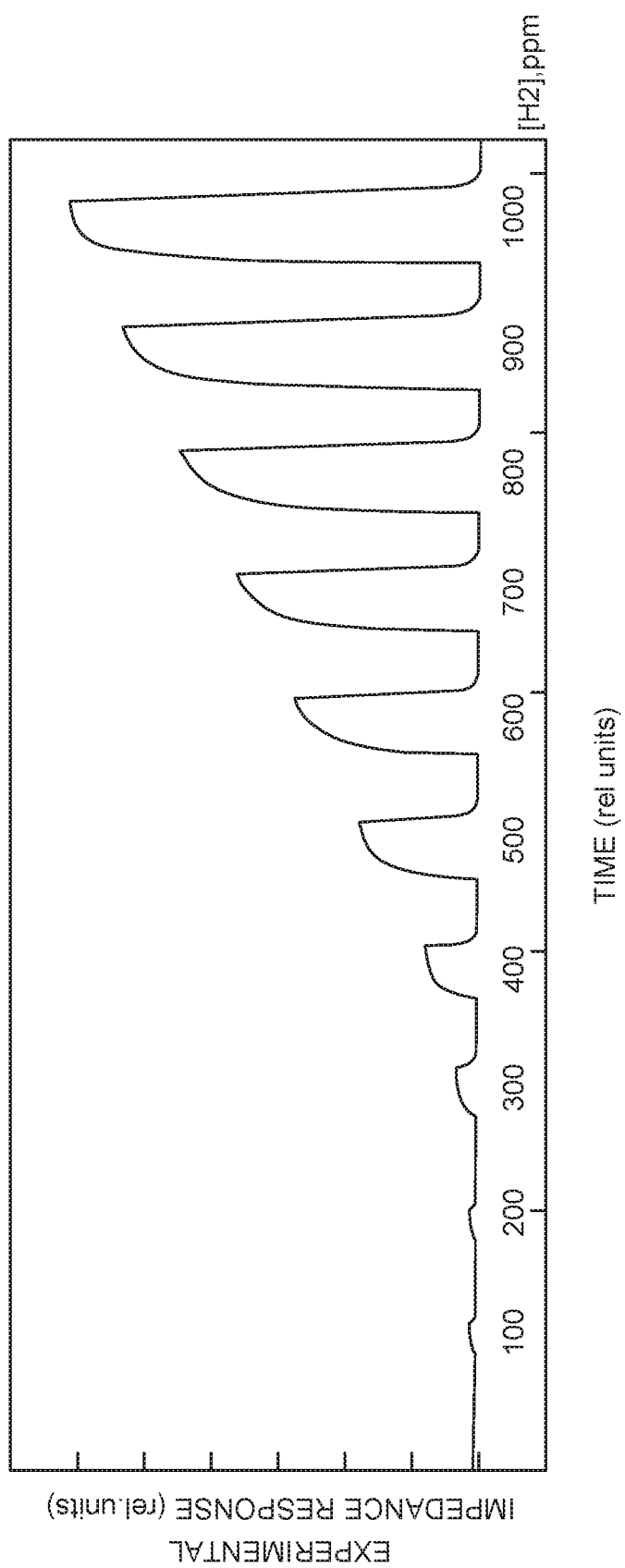
FIG. 23A illustrates a graphical illustration of a measured impedance response of a sensor to different concentrations of hydrogen gas at a third operation frequency of the sensor in accordance with one embodiment.

FIG. 23A illustrates the measured impedance response of the sensor to different H2 gas concentrations obtained at a third operation frequency of the sensor. For example, the third operation frequency may be about 99 kHz. The shape of the impedance response of the sensor is approximately an exponential shape that is visually different from the resistance response of the same semiconducting metal oxide upon exposure to increasing concentrations of H2 gas in air as illustrated in FIG. 5. Additionally, the exponential shape of the impedance response can be alternatively described by the power law equation Eq. (2). For example, a resistance response of the metal oxide sensor to increasing H2 concentrations in air of FIG. 23A can also be described with the power law represented by Eq. (2) but with a different coefficient $K_{H2}$ representing the resistance sensitivity of the sensor to H2 gas. For example, the value of the coefficient $K_{H2}$ of the power law calculation in FIG. 23A may be less than the value of the coefficient $K_{H2}$ of the power law calculation of the impedance response of FIG. 22A, and less than the value of the coefficient $K_{H2}$ of the power law calculation in FIG. 21A.

Figure 23B:
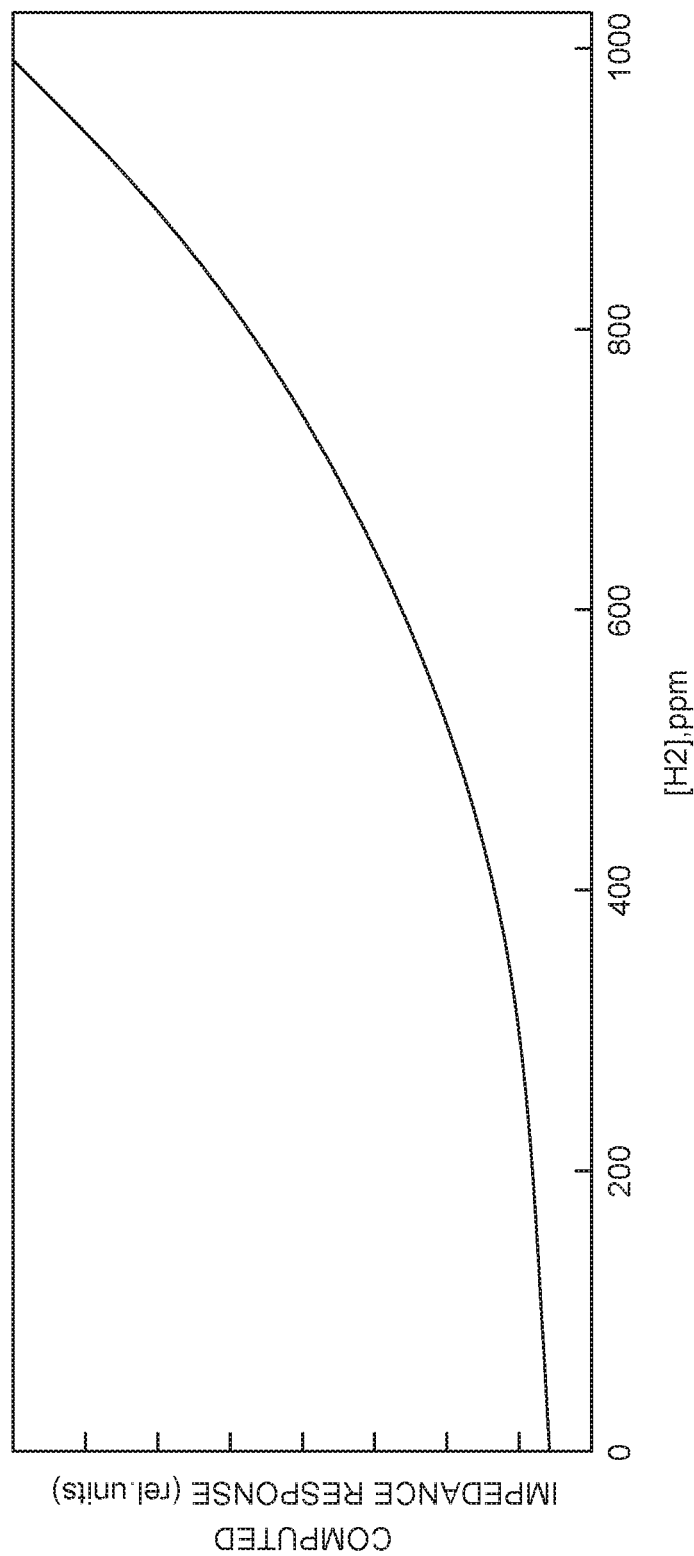
FIG. 23B illustrates a graphical illustration of a calculated impedance response of the sensor of FIG. 23A in accordance with one embodiment.

FIG. 23B illustrates the calculated resistance of the impedance response of the sensor of FIG. 23A. A visual comparison of the shapes of the responses illustrated in FIG. 23A and FIG. 23B demonstrates the exponential shape of the measured impedance response of the sensor. For example, the different coefficient $K_{H2}$ effects the shape of the sensor impedance response.

Figure 24:
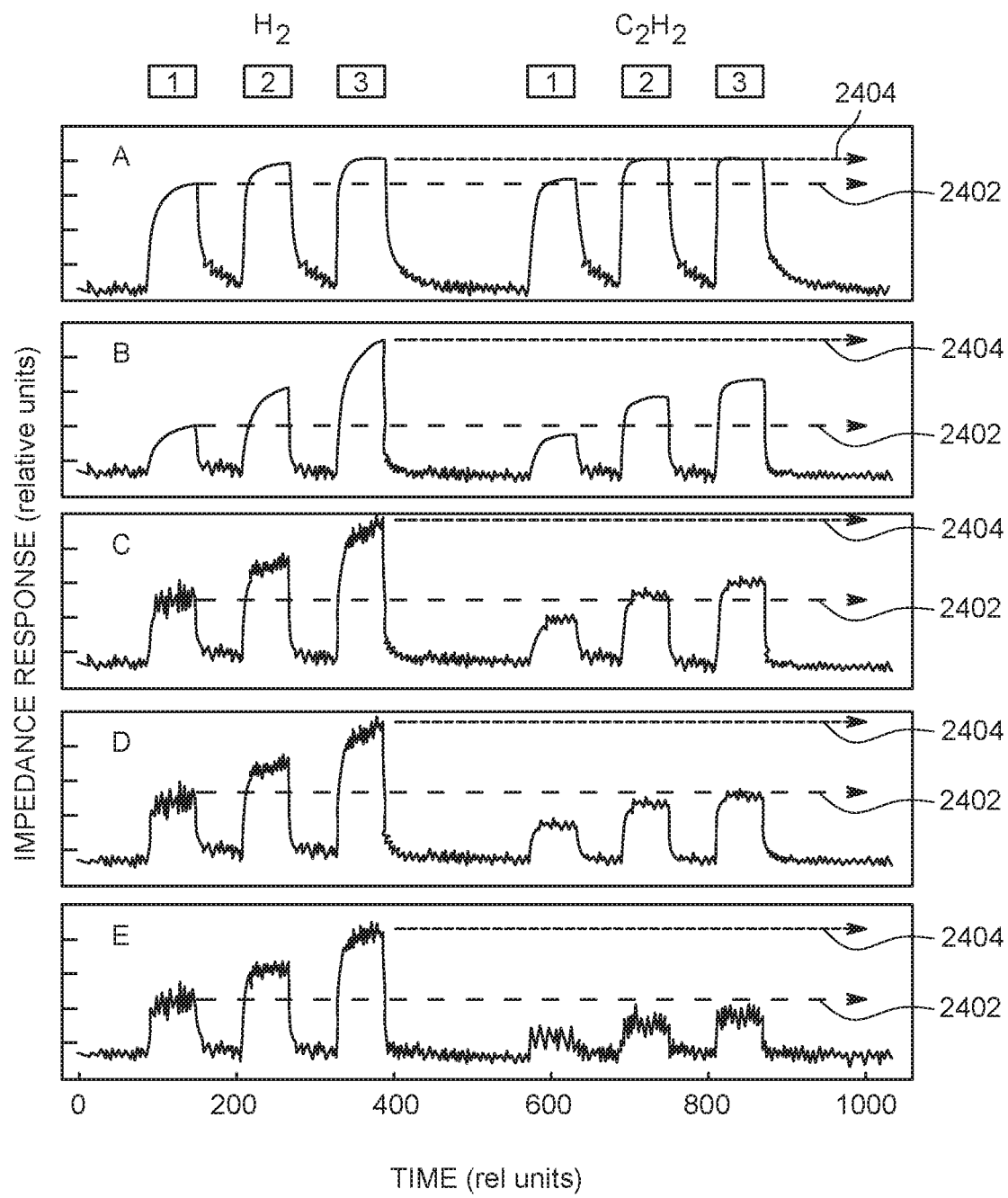
FIG. 24 illustrates a graphical illustration of frequency-dependent response patterns in accordance with one embodiment.

FIG. 24 illustrates an exemplary detection of hydrogen H2 and acetylene C2H2 diluted with air using an impedance sensor of this invention. The sensor utilized a semiconducting metal oxide as a sensing material (e.g., the sensing material 308). The semiconducting metal oxide was tin dioxide SnO2. Concentrations of H2 were generated at parts per million (ppm) levels such as 10 ppm (1), 15 ppm (2), and 20 ppm (3) and concentrations of C2H2 were generated at ppm levels such as 1000 ppm (1), 3000 ppm (2), and 5000 ppm (3) using a computer-controlled gas dilution and mixing system. The gas concentrations were presented to the sensor in sequence with a blank (clean air) between exposures to gases. The sensor was positioned in a low-dead volume gas flow cell. Results depicted in FIG. 24 illustrate detection of hydrogen H2 and acetylene C2H2 at different frequencies. For example, Graph A illustrates the sensor response at 8 kHz, Graph B illustrates the sensor response at 20 kHz, Graph C illustrates the sensor response at 50 kHz, Graph D illustrates the sensor response at 70 kHz, and Graph E illustrates the sensor response at 80 kHz.

Each Graph A-E includes two horizontal dotted lines 2402, 2404. The line 2402 highlights the response magnitude of the sensor to the lowest tested H2 concentration of 10 ppm (1) and compares this response magnitude with the response magnitude of the sensor to tested C2H2 concentrations. The line 2404 highlights the response magnitude of the sensor to the highest tested H2 concentration of 20 ppm (3) and compares this response magnitude with the response magnitude of the sensor to the tested C2H2 concentrations. Graph A demonstrates that at one illustrated frequency (8 kHz), the sensor response has similar magnitudes to H2 and C2H2 as highlighted by both lines 2402, 2404. However, as demonstrated in Graphs B-E, the response magnitude to C2H2 progressively decreases relative to the response magnitude to H2 at other illustrated frequencies. Thus, operation of the impedance sensor at different frequencies provides different response patterns to H2 and C2H2 where the relative response magnitudes to H2 and C2H2 are varied depending on the detection frequency. In one embodiment, the differences in the response patterns allows selection of an appropriate optimized single frequency with the relatively small effects of one gas when another gas is measured relative to selecting an alternative frequency. Such single optimized frequency is further used for sensing using a conventional sensor or a multivariable sensor. In another embodiment, the difference in the response patterns allows for the selection of appropriate several frequencies with the diverse effects of one gas when another gas is measured to perform further a multivariate analysis and is fully discriminate between two gases.

Figure 25A:
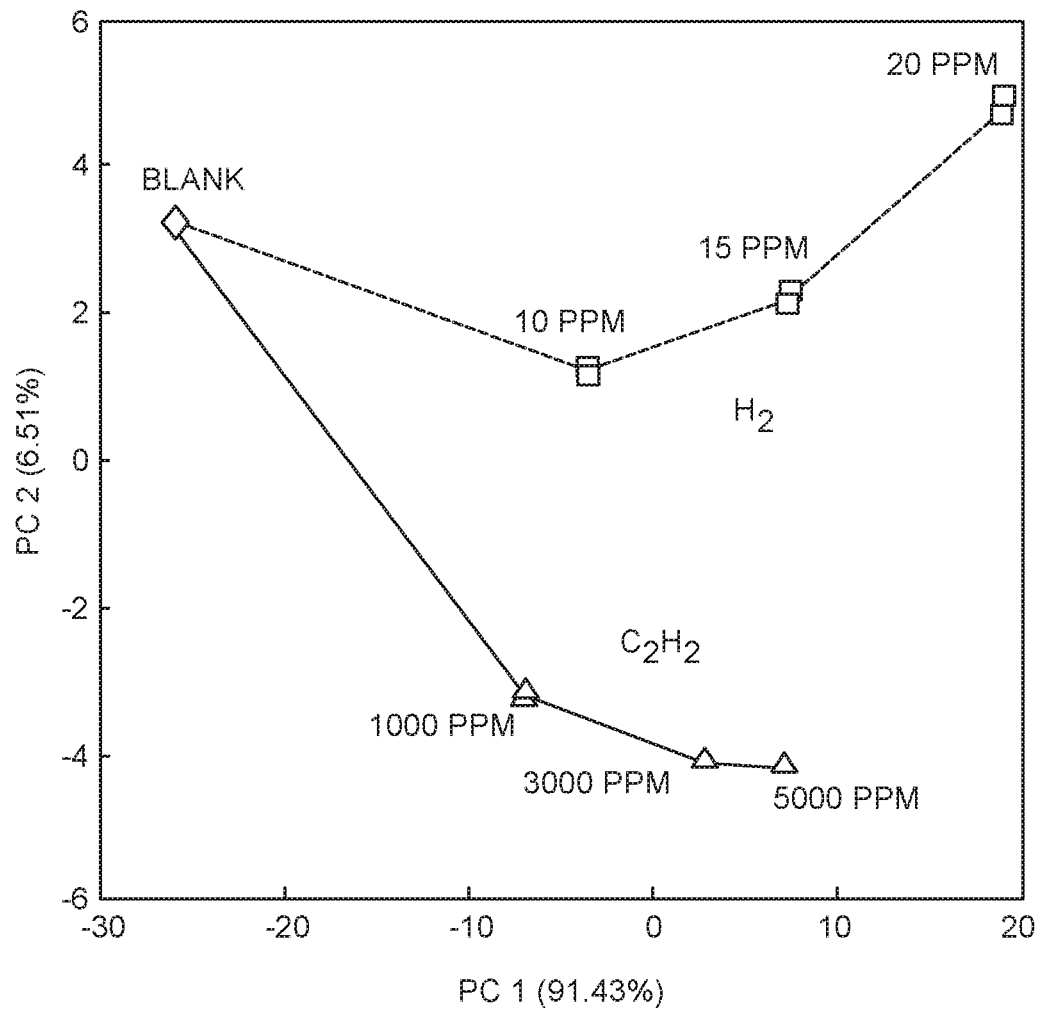
FIG. 25A illustrates a two-dimensional result of principal components analysis of frequency-dependent response patterns in accordance with one embodiment.
Figure 25B:
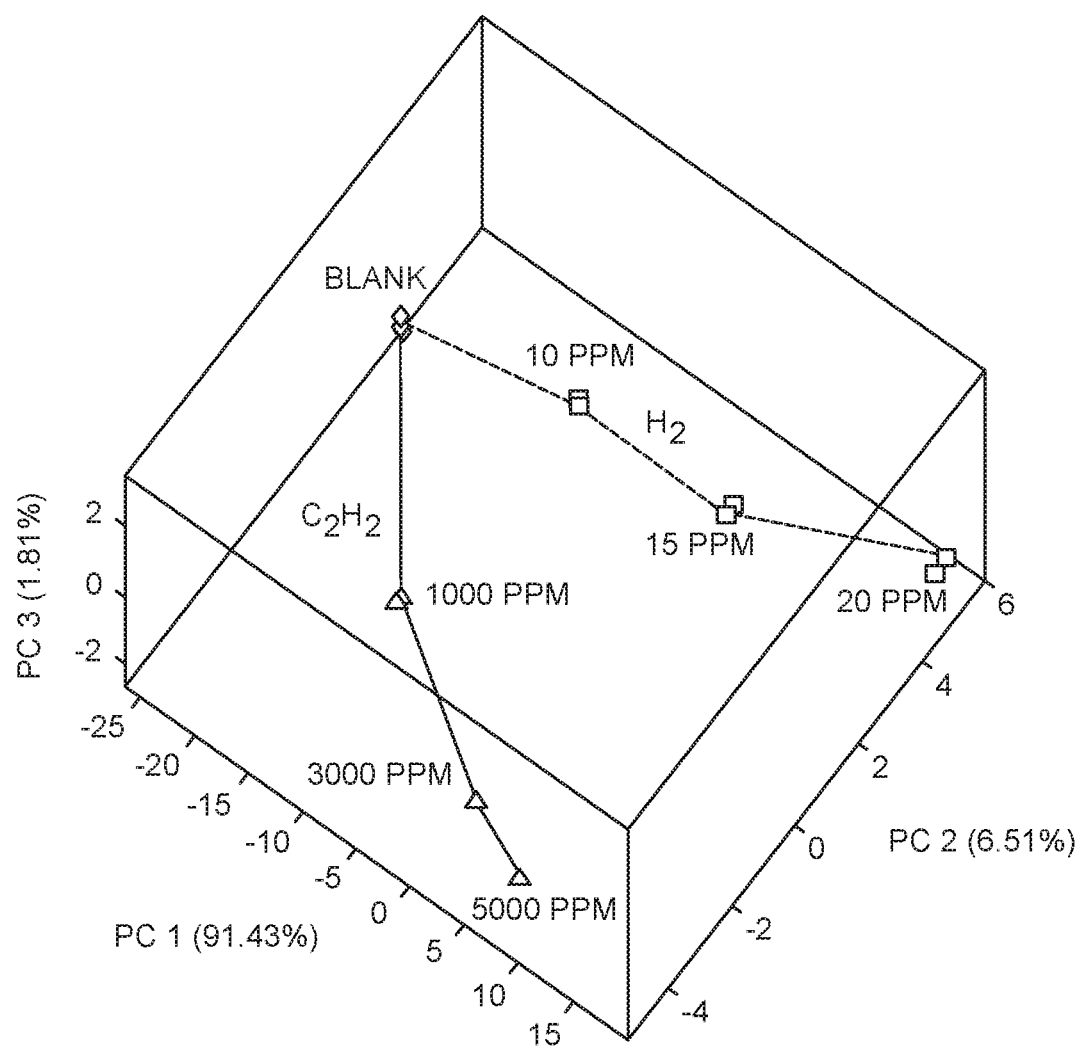
FIG. 25B illustrates a three-dimensional result of principal components analysis of frequency-dependent response patterns in accordance with one embodiment.

FIGS. 25A and 25B illustrate the results of principal components analysis (PCA) of frequency-dependent response patterns of an impedance sensor to H2 and C2H2 exposures at different concentrations. FIG. 25A illustrates a two-dimensional plot of a first principal component (PC1) versus a second principal component (PC2). Score plots of PC's visualize the response pattern of the sensor to different gases. Such plots illustrate that PCA response of a single impedance sensor based on a SnO2 sensing material start from the response to a blank (clean air) and is further directed into different directions that are dependent on the type of detected gas. FIG. 25B illustrates a three-dimensional plot of the PC1 versus the PC2 versus a third principal component (PC3). FIG. 25B illustrates that PCA response of a single impedance sensor based on a SnO2 sensing material has a high response dimensionality such as three dimensions. The higher the response dimensionality, the differentiation between the gases improves relative to lower response dimensionality.

In one embodiment of the subject matter described herein, a system for analysis of at least one analyte gas present in an insulating fluid of an electrical transformer includes a gas sensor configured to be in operational contact with at least one analyte gas from an insulating fluid and to provide multiple responses from the sensor. The system includes one or more processors configured to receive the multiple responses from the sensor during exposure of the sensor to the at least one analyte gas from the insulating fluid. The multiple responses representative of a concentration of the at least one analyte gas present in the insulating fluid. The one or more processors are configured to select one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

Optionally, the insulating fluid is transformer oil.

Optionally, the gas sensor is a multivariable gas sensor.

Optionally, the gas sensor includes one or more of an impedance sensor, a photonic sensor, an electronic sensor, or a hybrid sensor.

Optionally, the gas sensor has a sensing material that includes one or more of a metal oxide material, a composite material, a semiconducting material, an inorganic material, an organic material, a polymeric material, a nano-composite material, or a formulated material.

Optionally, the sensor is configured to be in operational contact with the insulating fluid by one or more of immersing the gas sensor in the insulating fluid or placing the sensor in a gas phase sample, wherein the gas phase sample is one or more of extracted from or representative of a dissolved gas content in the insulating fluid.

Optionally, the gas sensor is a sensor array.

Optionally, the at least one analyte gas includes one or more of H2, C2H2, CH4, C2H6, C2H4, CO or CO2.

Optionally, the at least one analyte gas includes one or more fault gases used for transformer diagnostics.

Optionally, the multiple responses from the sensor differ by one or more of sensor operating frequency, sensor operating wavelength, sensor operating temperature, sensor operating voltage, sensor operating power, or sensor operating polarization.

Optionally, the analysis of the at least one analyte gas present in the insulating fluid of the electrical transformer is performed one or more of online, inline, or offline.

Optionally, the sensor is configured to perform dissolved gas analysis (DGA) in transformer oil.

Optionally, the electrical transformer is installed one or more of below a ground level, above the ground level, or near to the ground level.

Optionally, the gas sensor is configured to operate at a temperature of at least 50° C. above an ambient temperature.

In one embodiment of the subject matter described herein, a method for analyzing at least one analyte gas present in an insulating fluid of an electrical transformer includes providing multiple responses from a multivariable gas sensor configured to be in operational contact with insulating fluid having at least one analyte gas. The method includes receiving with one or more processors the multiple responses from the sensor during exposure of the sensor to the insulating fluid. The multiple responses representative of a concentration of the at least one analyte gas present in the insulating fluid. The method includes selecting with the one or more processors one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

Optionally, the insulating fluid is transformer oil.

Optionally, the multivariable gas sensor includes one or more of an impedance sensor, a photonic sensor, an electronic sensor, or a hybrid sensor.

Optionally, the multivariable gas sensor has a sensing material that includes one or more of a metal oxide material, a composite material, a semiconducting material, an inorganic material, an organic material, a polymeric material, a nano-composite material, or a formulated material.

Optionally, the sensor is configured to be in operational contact with the insulating fluid by one or more of immersing the multivariable gas sensor in the insulating fluid or placing the sensor in a headspace of the insulating fluid.

Optionally, the multivariable gas sensor is a sensor array.

Optionally, the at least one analyte gas includes one or more of $H_2$, $C_2H_2$, $CH_4$, $C_2H_6$, $C_2H_4$, $CO$, or $CO_2$.

Optionally, the at least one analyte gas includes one or more fault gases to be used for transformer diagnostics.

Optionally, the multiple responses from the sensor differ by one or more of sensor operating frequency, sensor operating wavelength, sensor operating temperature, sensor operating voltage, sensor operating power, or sensor operating polarization.

Optionally, the analysis of the at least one analyte gas present in the insulating fluid of the electrical transformer is performed one or more of online, inline, or offline.

Optionally, the sensor is configured to perform dissolved gas analysis (DGA) in transformer oil.

Optionally, the method further includes installing the electrical transformers one or more of below a ground level, above the ground level, or near to the ground level.

Optionally, the method further includes operating the multivariable gas sensor at a temperature of at least 50° C. above an ambient temperature.

In one embodiment of the subject matter described herein, a system includes an impedance gas sensor configured to be in contact with a sample having one or more analyte gases therein. The impedance sensor including electrodes and a sensing region circuit having a sensing material. The electrodes configured to apply electrical stimuli to the sensing material at one or more different frequencies. The system includes one or more processors configured to receive an electrical signal from the sensor that is representative of an impedance of the sensing material during exposure of the sensing material to the sample at the one or more different frequencies. The impedance is representative of a concentration of an analyte gas of interest of the one or more analyte gases in the sample. The one or more processors are configured to select a frequency of the one or more different frequencies at which the electrodes of the sensor are to apply the electrical stimuli to the sensing material based on the analyte gas of interest to be sensed by the sensor. The one or more processors are configured to select one or more responses from the sensor that provide one or more of rejection of one or more interfering gases, resolution between at least two gases, improved low detection range of the one or analyte gases, improved high detection range of the one or more analyte gases, improved response linearity of the one or more of the analyte gases, improved dynamic range of measurements of the one or more of the analyte gases, or one or more combinations thereof as compared to non-selected responses from the sensor.

In one embodiment of the subject matter described herein, a method includes receiving with one or more processors an electrical signal from an impedance gas sensor that is in contact with a sample having one or more analyte gases therein. The impedance sensor including electrodes and a sensing region circuit having a sensing material that receives electrical stimuli at one or more different frequencies from the electrodes. A frequency of the one or more different frequencies at which the electrodes of the sensor apply the electrical stimuli to the sensing material is based on an analyte gas of interest to be sensed by the sensor of the one or more analyte gases. The method includes determining a concentration of the analyte gas of interest of the one or more analyte gases in the sample based on the electrical signal received from the sensor. The electrical signal is representative of an impedance of the sensing material during exposure of the sensing material to the sample at one or more different frequencies. The impedance of the sensing material indicates a concentration of the analyte gas of interest in the sample.

In one embodiment of the subject matter described herein, a system includes an impedance gas sensor configured to be in contact with a sample having one or more analyte gases therein. The impedance sensor includes a sensing material that receives electrical stimuli at one or more frequencies. The system includes one or more processors configured to receive at electrical signal from the sensor that is representative of an impedance of the sensing material during exposure of the sensing material to the sample at the one or more different frequencies. The impedance is representative of a concentration of an analyte gas of interest of the one or more analyte gases in the sample. The one or more processors are configured to change the one or more frequencies at which the electrical stimuli are applied to the sensing material to change a sensitivity of the sensing material to different gases of the one or more analyte gases. The one or more processors are configured to select one or more responses from the sensor that provide one or more of rejection of one or more interfering gases, resolution between at least two gases, improved low detection range of the one or more analyte gases, improved high detection range of the one or more analyte gases, improved response linearity of the one or more analyte gases, improved dynamic range of measurements of the one or more analyte gases, or one or more combinations thereof as compared to non-selected responses from the sensor.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system for analysis of at least one analyte gas present in an insulating fluid of an electrical transformer, comprising:
   a gas sensor configured to be in operational contact with at least one analyte gas from an insulating fluid and to provide multiple responses from the sensor responsive to electrodes applying electrical stimuli to a sensing material of the gas sensor with an alternating current at one or more frequencies, wherein the gas sensor is immersed in the insulating fluid or placed in a gas phase sample, and wherein the electrodes are coupled with or disposed in the sensing material and are connected to a substrate of the gas sensor; and
   one or more processors configured to receive the multiple responses from the sensor during exposure of the sensor to the at least one analyte gas from the insulating fluid, the multiple responses representative of a concentration of the at least one analyte gas present in the insulating fluid during exposure of the at least one analyte gas at the one or more different frequencies,
   and wherein the one or more processors are configured to select one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

2. The system of claim 1, wherein the insulating fluid is transformer oil.

3. The system of claim 1, wherein the gas sensor is a multivariable gas sensor.

4. The system of claim 1, wherein the gas sensor includes one or more of an impedance sensor, a photonic sensor, an electronic sensor, or a hybrid sensor.

5. The system of claim 1, wherein the sensing material includes one or more of a metal oxide material, a composite material, a semiconducting material, an inorganic material, an organic material, a polymeric material, a nano-composite material, or a formulated material.

6. The system of claim 1, wherein the gas phase sample is one or more of extracted from or representative of a dissolved gas content in the insulating fluid.

7. The system of claim 1, wherein the gas sensor is a sensor array.

8. The system of claim 1, wherein the at least one analyte gas includes one or more of H2, C2H2, CH4, C2H6, C2H4, CO, or CO2.

9. The system of claim 1, wherein the at least one analyte gas includes one or more fault gases to be used for transformer diagnostics.

10. The system of claim 1, wherein the multiple responses from the sensor differ by one or more of sensor operating frequency, sensor operating wavelength, sensor operating temperature, sensor operating voltage, sensor operating power, or sensor operating polarization.

11. The system of claim 1, wherein the analysis of the at least one analyte gas present in the insulating fluid of the electrical transformer is performed one or more of online, inline, or offline.

12. The system of claim 1, wherein the gas sensor is configured to perform dissolved gas analysis (DGA) in transformer oil.

13. The system of claim 1, wherein the electrical transformer is installed one or more of below a ground level, above the ground level, or near to the ground level.

14. The system of claim 1, wherein the gas sensor is configured to operate at a temperature of at least 50.degree. C. above an ambient temperature.

15. A method for analyzing at least one analyte gas present in an insulating fluid of an electrical transformer, the method comprising:
providing multiple responses from a multivariable gas sensor configured to be in operational contact with insulating fluid having at least one analyte gas responsive to electrodes applying electrical stimuli to a sensing material of the multivariable gas sensor with an alternating current at one or more frequencies, wherein the multivariable gas sensor is immersed in the insulating fluid or placed in a headspace of the insulating fluid, and wherein the electrodes are coupled with or disposed in the sensing material and are connected to a substrate of the multivariable gas sensor;
receiving with one or more processors the multiple responses from the sensor during exposure of the sensor to the insulating fluid, the multiple responses representative of a concentration of the at least one analyte gas present in the insulating fluid during exposure of the at least one analyte gas at the one or more different frequencies; and
selecting with the one or more processors one or more responses of the multiple responses from the sensor that provide rejection of one or more interfering gases, resolution between at least two gases, improved low detection range of the at least one analyte gas, improved high detection range of the at least one analyte gas, improved response linearity of the at least one analyte gas, improved dynamic range of measurements of the at least one analyte gas, or one or more combinations thereof as compared to non-selected responses from the sensor.

16. The method of claim 15, wherein the multivariable gas sensor includes one or more of an impedance sensor, a photonic sensor, an electronic sensor, or a hybrid sensor.

17. A system comprising:
an impedance gas sensor configured to be in contact with a sample having one or more analyte gases therein, the impedance sensor including electrodes and a sensing region circuit having a sensing material, the electrodes configured to apply electrical stimuli to the sensing material at one or more different frequencies, wherein the impedance gas sensor is immersed in an insulating fluid or placed in a gas phase sample, and wherein the electrodes are coupled with or disposed in the sensing material and are connected to a substrate of the impedance gas sensor; and
one or more processors configured to receive an electrical signal from the sensor that is representative of an impedance of the sensing material during exposure of the sensing material to the sample at the one or more different frequencies, the impedance representative of a concentration of an analyte gas of interest of the one or more analyte gases in the sample,
wherein the one or more processors are configured to select a frequency of the one or more different frequencies at which the electrodes of the sensor are to apply the electrical stimuli to the sensing material based on the analyte gas of interest to be sensed by the sensor; and
wherein the one or more processors are configured to select one or more responses from the sensor that provide one or more of rejecting of one or more interfering gases, resolution between at least two gases, improved low detection range of the one or more analyte gases, improved high detection range of the one or more of the analyte gases, improved response linearity of the one or more of the analyte gases, improved dynamic range of measurements of the one or more of the analyte gases, or one or more combinations thereof as compared to non-selected responses from the sensor.

18. A method comprising:
receiving with one or more processors an electrical signal from an impedance gas sensor that is in contact with a sample having one or more analyte gases therein, the impedance sensor including electrodes and a sensing region circuit having a sensing material that receives electrical stimuli at one or more different frequencies from the electrodes, wherein a frequency of the one or more different frequencies at which the electrodes of the sensor apply the electrical stimuli to the sensing material is based on an analyte gas of interest to be sensed by the sensor of the one or more analyte gases, and wherein the impedance gas sensor is immersed in an insulating fluid or placed in a gas phase sample, and wherein the electrodes are coupled with or disposed in the sensing material and are connected to a substrate of the impedance gas sensor; and
determining a concentration of the analyte gas of interest of the one or more analyte gases in the sample based on the electrical signal received from the sensor, the electrical signal representative of an impedance of the sensing material during exposure of the sensing material to the sample at the one or more different frequencies,
wherein the impedance of the sensing material indicates a concentration of the analyte gas of interest in the sample.

19. A system comprising:
an impedance gas sensor configured to be in contact with a sample having one or more analyte gases therein, the impedance sensor including a sensing material that receives electrical stimuli at one or more frequencies responsive to electrodes applying the electrical stimuli to the sensing material with an alternating current at the one or more frequencies, wherein the impedance sensor is immersed in an insulating fluid or placed in a gas phase sample, and wherein the electrodes are coupled with or disposed in the sensing material and are connected to a substrate of the gas sensor; and
one or more processors configured to receive an electrical signal from the sensor that is representative of an impedance of the sensing material during exposure of the sensing material to the sample at the one or more different frequencies, the impedance representative of a concentration of an analyte gas of interest of the one or more analyte gases in the sample,
wherein the one or more processors are configured to change the one or more frequencies at which the electrical stimuli are applied to the sensing material to change a sensitivity of the sensing material to different gases of the one or more analyte gases; and
wherein the one or more processors are configured to select one or more responses from the sensor that provide one or more of rejecting of one or more interfering gases, resolution between at least two gases, improved low detection range of the one or more analyte gases, improved high detection range of the one or more analyte gases, improved response linearity of the one or more analyte gases, improved dynamic range of measurements of the one or more analyte gases, or one or more combinations thereof as compared to non-selected responses from the sensor.

\* \* \* \* \*